US012162846B2

United States Patent
Tieu et al.

(10) Patent No.: US 12,162,846 B2
(45) Date of Patent: Dec. 10, 2024

(54) DRP-1 INHIBITORS AS THERAPEUTIC AGENTS

(71) Applicants: Kim Tieu, Miami, FL (US); Adel Nefzi, Miami, FL (US); Stephen Black, Miami, FL (US)

(72) Inventors: Kim Tieu, Miami, FL (US); Adel Nefzi, Miami, FL (US); Stephen Black, Miami, FL (US)

(73) Assignee: THE FLORIDA INTERNATIONAL UNIVERSITY BOARD OF TRUSTEES, Miami, FL (US)

( * ) Notice: Subject to any disclaimer, the term of this patent is extended or adjusted under 35 U.S.C. 154(b) by 0 days.

(21) Appl. No.: 18/433,879

(22) Filed: Feb. 6, 2024

(65) Prior Publication Data

US 2024/0294481 A1 Sep. 5, 2024

Related U.S. Application Data

(60) Provisional application No. 63/444,682, filed on Feb. 10, 2023.

(51) Int. Cl.
| | |
|---|---|
| *C07D 277/42* | (2006.01) |
| *A61K 31/496* | (2006.01) |
| *A61P 11/00* | (2006.01) |
| *A61P 25/16* | (2006.01) |
| *C07D 417/12* | (2006.01) |

(52) U.S. Cl.
CPC .......... *C07D 277/42* (2013.01); *A61K 31/496* (2013.01); *A61P 11/00* (2018.01); *A61P 25/16* (2018.01); *C07D 417/12* (2013.01)

(58) Field of Classification Search
CPC ..... C07D 277/42; C07D 417/12; A61P 11/00; A61P 25/16; A61K 31/496
See application file for complete search history.

(56) References Cited

U.S. PATENT DOCUMENTS

| | | |
|---|---|---|
| 9,243,232 B2 | 1/2016 | Mochly-Rosen et al. |
| 11,229,629 B2 | 1/2022 | Wu et al. |
| 2013/0053321 A1 | 2/2013 | Mochly-Rosen et al. |

FOREIGN PATENT DOCUMENTS

| | | | | |
|---|---|---|---|---|
| WO | 01/10848 A2 | 2/2001 | | |
| WO | 2014/179144 A1 | 11/2014 | | |
| WO | WO-2015168518 A1 | * 11/2015 | ........... | C07D 277/42 |
| WO | WO-2021248231 A1 | * 12/2021 | ............. | A61P 35/00 |

OTHER PUBLICATIONS

Archer, Stephen L. "Mitochondrial Dynamics—Mitochondrial Fission and Fusion in Human Diseases." The New England Journal of Medicine 369(23):2236-2251, (Year: 2015).

* cited by examiner

*Primary Examiner* — Clinton A Brooks
*Assistant Examiner* — Josmalen M. Ramos-Lewis
(74) *Attorney, Agent, or Firm* — SALIWANCHIK, LLOYD & EISENSCHENK

(57) ABSTRACT

The subject invention provides compounds as Drp1 inhibitors, compositions comprising a Drp1 inhibitor, and methods for inhibiting Drp1 protein using the Drp1 inhibitors. Further provided are methods for treating and/or preventing a disease or condition associated with mitochondrial dysfunction, oxidative stress, inflammation and/or autophagy. Advantageously, the compounds and compositions of the subject invention can also be used to treat a variety of other conditions including, for example, autoimmune disorders, disorders of the nervous system, and cardiovascular disorders.

2 Claims, 8 Drawing Sheets

CTS-2444-19
Chemical Formula: $C_{26}H_{28}Cl_2N_4OS$
Molecular Weight: 515.50

Inhibition: 40.81%

CTS-2444-20
Chemical Formula: $C_{21}H_{34}N_4OS$
Molecular Weight: 390.59

Inhibition: 40.55%

CTS-2444-32
Chemical Formula: $C_{22}H_{34}N_4OS$
Molecular Weight: 402.60

Inhibition: 45.78%

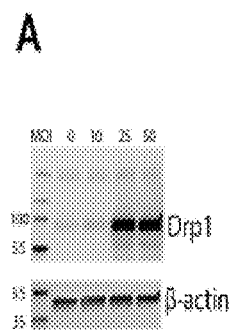
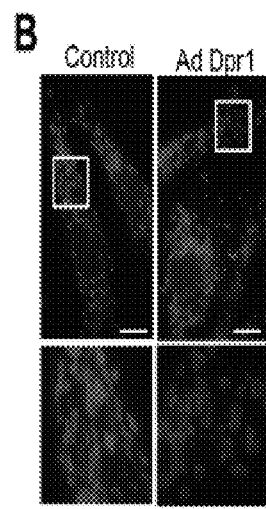
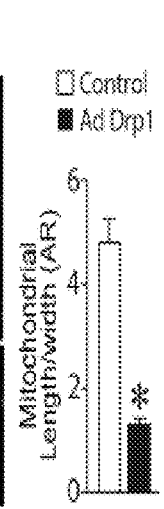
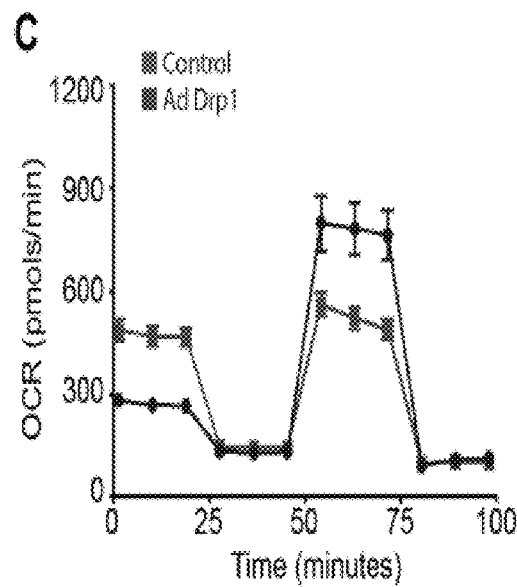
FIG. 2A                FIG. 2B                                FIG. 2C
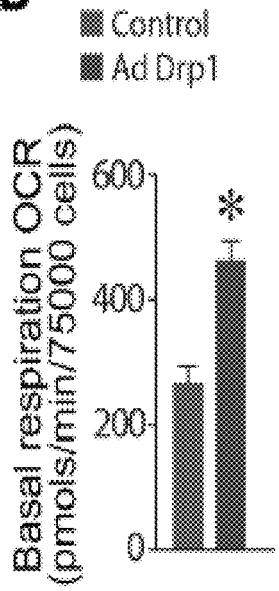
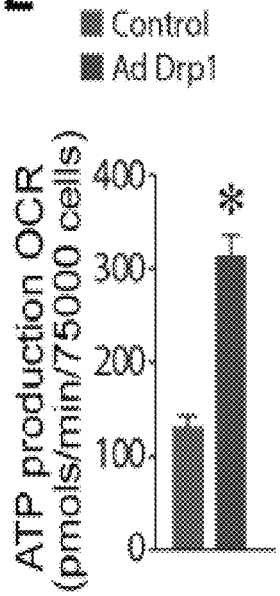
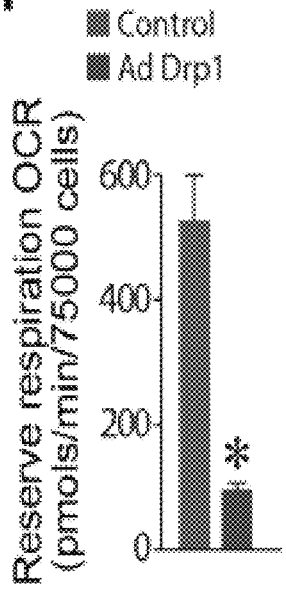
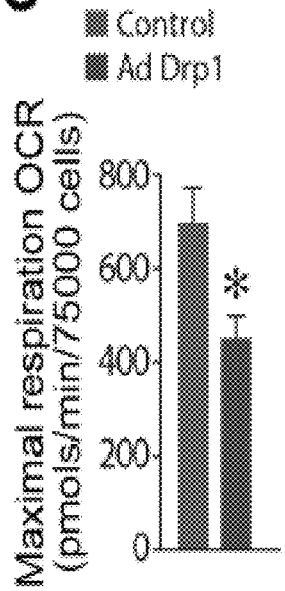
FIG. 2D            FIG. 2E            FIG. 2F            FIG. 2G

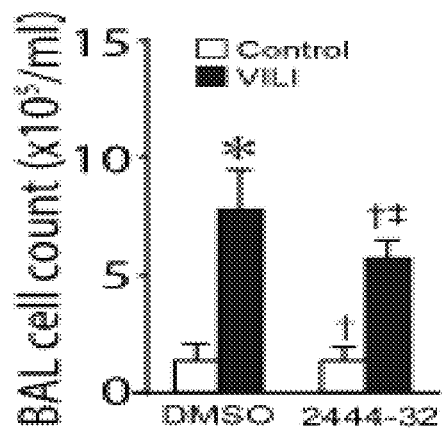
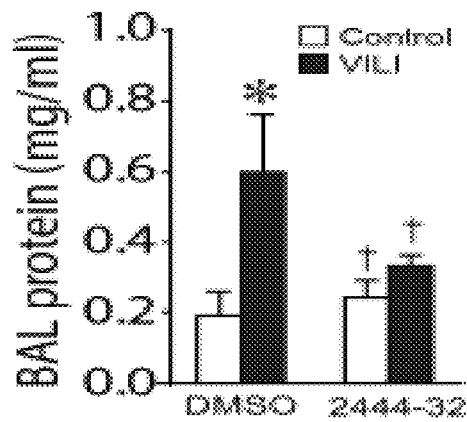
FIG. 5B  FIG. 5C
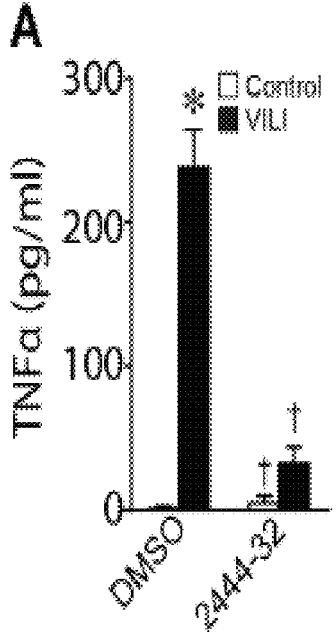
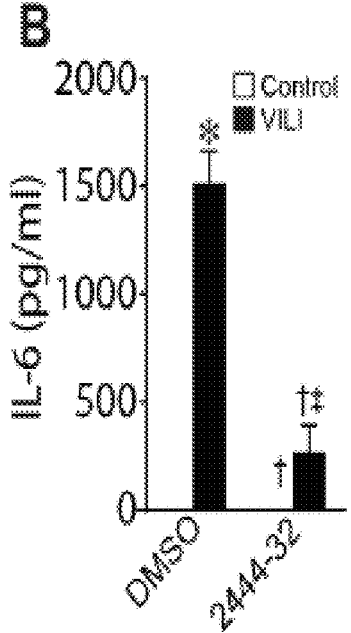
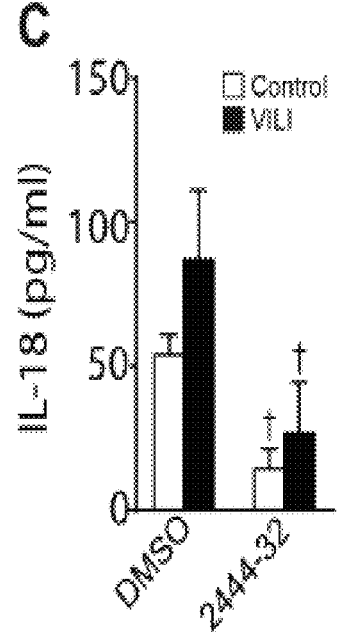
FIG. 6A  FIG. 6B  FIG. 6C

DRP-1 INHIBITORS AS THERAPEUTIC AGENTS

CROSS-REFERENCE TO RELATED APPLICATION

This application claims the benefit of U.S. Provisional Application Ser. No. 63/444,682 filed Feb. 10, 2023, which is hereby incorporated by reference herein in its entirety.

GOVERNMENT SUPPORT

This invention was made with government support under ES030523 awarded by the National Institutes of Health. The government has certain rights in the invention.

BACKGROUND OF INVENTION

Mitochondria are essential to the maintenance of normal neuronal function and viability through regulation of key processes such as energy production; calcium homeostasis; intracellular transport; and neurotransmitter release and reuptake. Mitochondria are highly dynamic organelles, and hence the term "mitochondrial dynamics" refers to the processes of fission, fusion and movement along microtubules that allow mitochondria to supply energy to other parts of the cell. A balance of fusion and fission is crucial not only to mitochondrial morphology, but also function and survival of cells.

Fission is a process to create smaller, more discrete mitochondria, which may be capable of generating reactive oxygen species, facilitating mitophagy, or accelerating cell proliferation. Fusion results in a more interconnected mitochondrial network that enhances communication with the endoplasmic reticulum. Fusion also allows diffusion of matrix content among mitochondria.

Both fission and fusion are mediated by a small number of highly conserved, guanosine triphosphatases (GTPases). Fission is mediated by dynamin related protein 1 (Drp1), a cytosolic protein that on activation translocates to the mitochondrial outer membrane (MOM) where Drp1 induces mitochondrial division by forming oligomeric chains wrapping around mitochondria. Drp1 is actively targeted to the MOM by non-GTPase receptor proteins such as mitochondrial fission protein 1 (Fis1), mitochondrial fission factor (MFF), and mitochondrial elongation factor 1. MiD49 and MiD51 are also MOM proteins that recruit Drp1. Assembly of the fission apparatus is assisted by the endoplasmic reticulum, which contacts the mitochondria, creating a microdomain for assembly of Drp1, MFF, and proapoptotic proteins.

The MOM mitofusin (Mfn1 and Mfn2) and the inner mitochondrial protein optic atrophy 1 (OPA-1) are responsible for mitochondrial fusion. Together, these proteins help to regulate mitochondrial morphology and function within cells, and to manage their response to metabolic stress.

Accumulating evidence indicates that perturbed mitochondrial dynamics is a pathogenic mechanism in a number of diseases and manipulating mitochondrial fission/fusion has been considered as a potential novel therapy for a wide range of diseases, including neurological disorders, cancer and pulmonary conditions. One therapeutic strategy is to block mitochondrial fission. Because Drp1 can bind to multiple downstream fission proteins to sever mitochondria, Drp1 is an attractive target.

One major drawback of current Drp1 inhibitors is their off-target effects. Mitochondrial division inhibitor (mdivi-1) was first identified as an inhibitor of mitochondrial division in yeast screens. Its protective effects mediated through blocking mitochondrial fission have been reported in a wide range of disease models. However, it has been shown that mdivi-1 is a weak and non-specific inhibitor of Drp1 GTPase. Also, this molecule was reported to be a reversible inhibitor of complex I and ROS production generated via reverse electron transfer mechanism.

P110 is a peptide-based inhibitor designed to interfere with the interaction of Drp1 with Fis1. In addition to blocking Drp1 translocation from the cytosol to mitochondria, P110 also partially inhibits the GTPase activity of Drp1. One limitation of using P110 as a therapeutic is its poor oral bioavailability due to the unfavorable physiological environment (pH, enzymes) and physical barriers in the gastrointestinal track. Indeed, in animal studies, P110-TAT was delivered through subcutaneous mini-osmotic pumps to bypass the gastric issue.

Dynasore is a non-competitive dynamin GTPase inhibitor. Dynasore is not a specific Drp1 inhibitor because it also blocks dynamin 1 and dynamin 2. Recently, through virtual and in silico screenings, Drpitor1 was identified as a Drp1 inhibitor. A congener of Drpitor1, Drpitor1a, was synthesized to remove the methoxymethyl group and reduce hydrolytic lability. Both molecules were demonstrated to reduce cell proliferation and suppress lung cancer tumor growth in a xenograft mouse model as well as to protect against cardiac ischemia-reperfusion injury. However, the structure of Drpitor1a is identical to ellipticine quinone, which has been shown to have antitumor activity most likely through DNA intercalation and topoisomerase II inhibition. These additional non-specific mechanisms raise concerns about their potential side-effects.

Thus, there is a need to develop methods for screening and identifying compounds that specifically inhibit Drp1 and prevent mitochondrial fission. There is also a need to develop methods for treating diseases and conditions related to mitochondrial fission.

BRIEF SUMMARY

The subject invention provides compounds that specifically inhibit Drp1. The subject invention also provides compositions comprising a compound that inhibits Drp1, and methods for inhibiting Drp1 and treating and/or preventing mitochondrial fission. The compounds and compositions of the subject invention can further be used to treat and/or prevent diseases and conditions associated with mitochondrial dysfunction, oxidative stress, inflammation and autophagy.

In one embodiment, the subject invention provides novel Drp1 inhibitors that are protective, for example, in acute lung injury models and Parkinson's disease models. Advantageously, the compounds have a direct effect on blocking Drp1 function.

In one embodiment, the subject invention provides compounds that inhibit Drp1 activity. In specific embodiments, the compounds have a structure of:

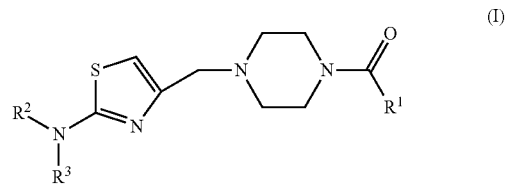

(I)

wherein $R^1$, $R^2$ and $R^3$ are independently selected from, for example, hydrogen, hydroxyl, alkyl, substituted alkyl, aryl, substituted aryl, heteroalkyl, substituted heteroalkyl, heteroaryl, substituted heteroaryl, cycloalkyl, substituted cycloalkyl, heterocycloalkyl, substituted heterocycloalkyl, cycloalkenyl, substituted cycloalkenyl, alkenyl, substituted alkenyl, alkynyl, alkoxyl, substituted alkoxyl, hydroxylalkyl, and substituted hydroxylalkyl.

In certain embodiments, $R^1$ is selected from

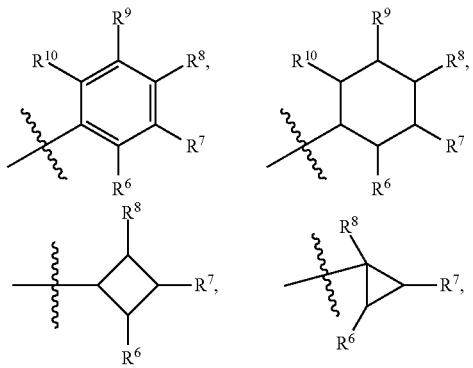

and $-CHR^4R^{11}$; and $R^2$ and $R^3$ are independently selected from

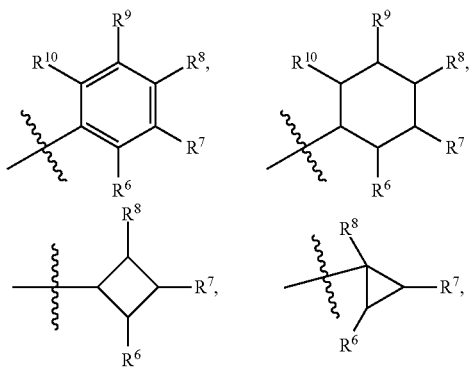

and $-CHR^5R^{12}$, wherein $R^4$ is selected from hydrogen, alkyl, substituted alkyl, aryl, substituted aryl, heteroalkyl, substituted heteroalkyl, heteroaryl, substituted heteroaryl, cycloalkyl, substituted cycloalkyl, heterocycloalkyl, substituted heterocycloalkyl, and $-OH$; $R^5$ is selected from hydrogen, alkyl, substituted alkyl, aryl, substituted aryl, heteroalkyl, substituted heteroalkyl, heteroaryl, substituted heteroaryl, cycloalkyl, substituted cycloalkyl, hydroxyl, acyl, and alkylamino; $R^6$, $R^7$, $R^8$, $R^9$, and $R^{10}$ are, at each occurrence, independently selected from hydrogen, halogen, alkyl, substituted alkyl, aryl, substituted aryl, alkoxyl, $-OH$, $-NR^{13}R^{14}$, and acyl; $R^{11}$ is selected from hydrogen, halogen, alkyl, substituted alkyl, aryl, substituted aryl, cycloalkyl, and substituted cycloalkyl, alkoxyl, $-OH$, $-NR^{13}R^{14}$, and acyl; and $R^{12}$ is selected from hydrogen, halogen, alkyl, substituted alkyl, aryl, substituted aryl, cycloalkyl, and substituted cycloalkyl, alkoxyl, $-OH$, $-NR^{13}R^{14}$, and acyl, wherein $R^{13}$ and $R^{14}$ are, at each occurrence, independently selected from hydrogen, alkyl, substituted alkyl, aryl, and substituted aryl.

In one embodiment, the compounds have a structure of:

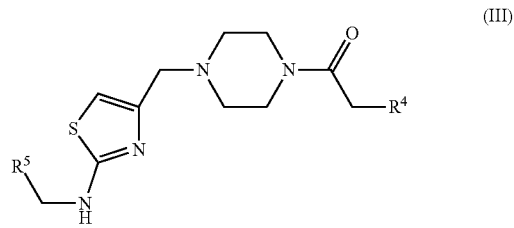

wherein $R^4$ and $R^5$ are independently selected from, for example, hydrogen, alkyl, substituted alkyl, aryl, substituted aryl, heteroalkyl, substituted heteroalkyl, heteroaryl, substituted heteroaryl, cycloalkyl, substituted cycloalkyl, heterocycloalkyl, substituted heterocycloalkyl, cycloalkenyl, substituted cycloalkenyl, alkenyl, substituted alkenyl, alkynyl, alkoxyl, acyl, alkylamino and hydroxyalkyl.

In a specific embodiment, the compounds are selected from

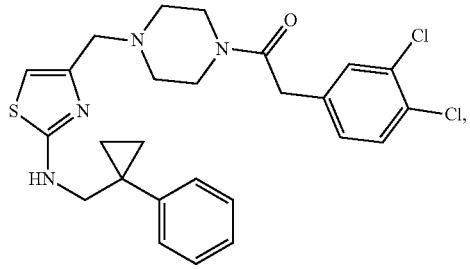

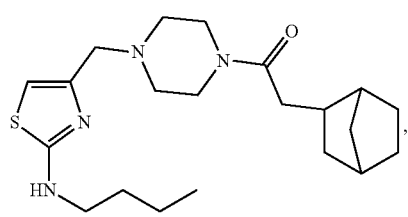

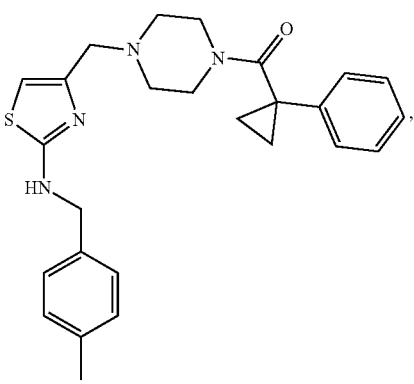

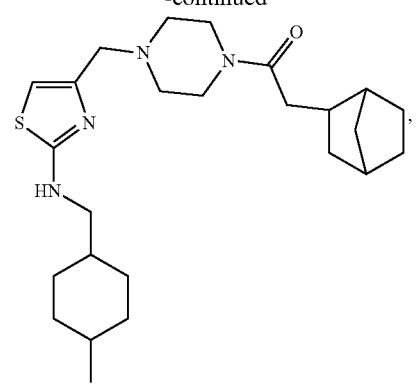
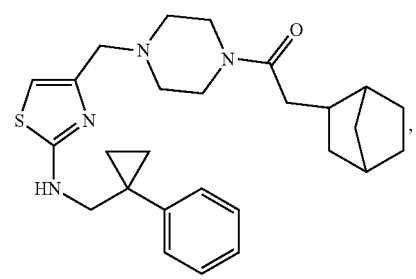
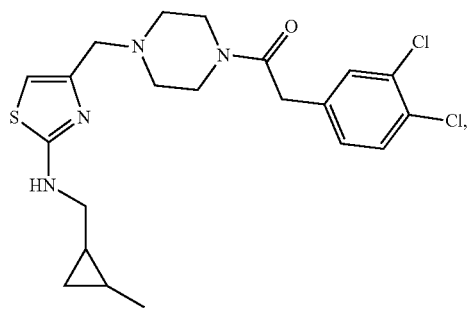
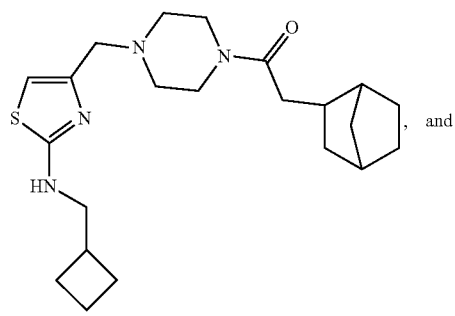, and
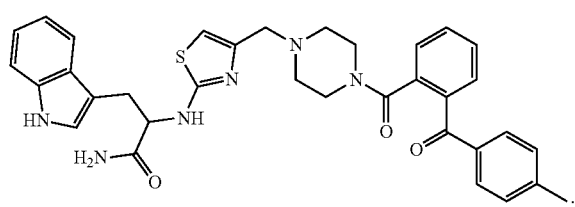
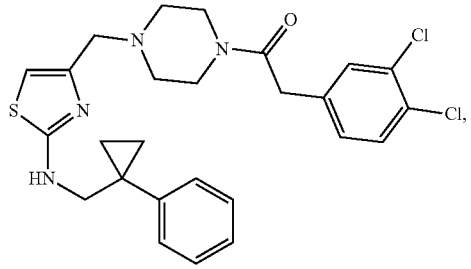
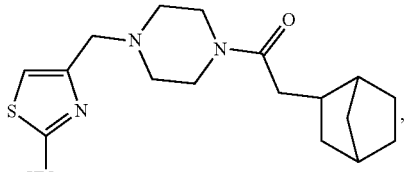
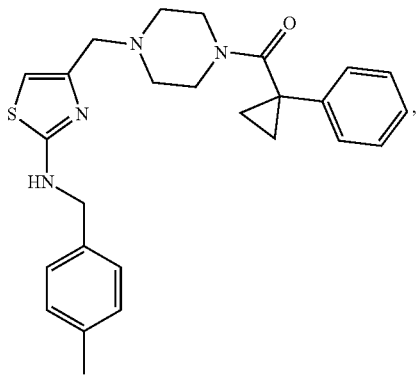
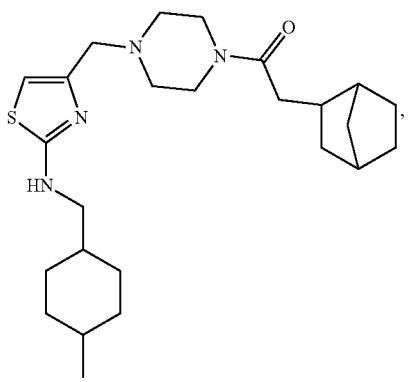
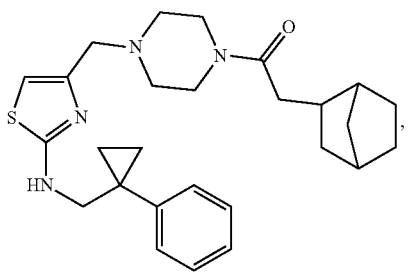
In one embodiment, the subject invention provides a composition comprising a Drp1 inhibitor and optionally, a pharmaceutically acceptable carrier. In a specific embodiment, the composition comprises a compound selected from

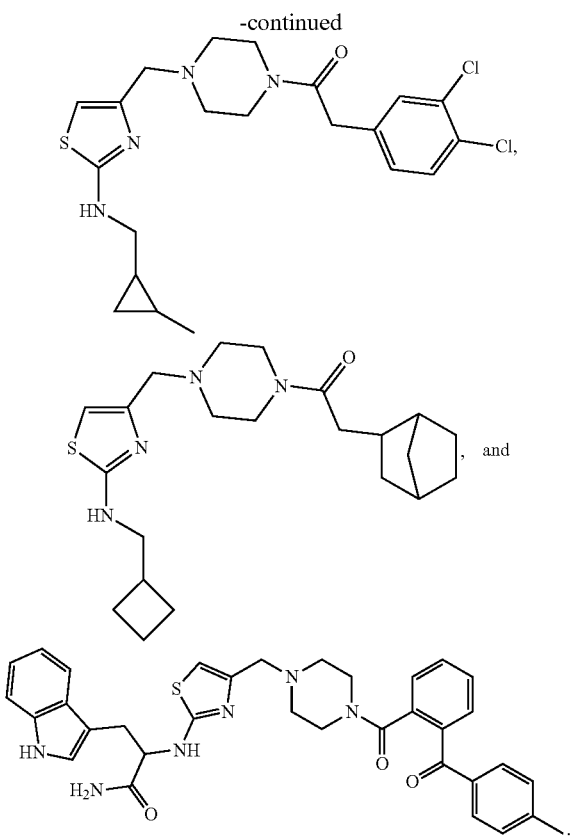

In one embodiment, the subject invention provides a method for treating a disease or condition, wherein the method comprises administering to a subject in need of such treatment a compound of the subject invention or a composition of the subject invention comprising the compound of the subject invention.

The diseases include, but are not limited to, neurodegenerative diseases such as Parkinson's disease, Alzheimer's disease, Huntington's disease and amyotrophic lateral sclerosis (ALS); neuropathies such as Charcot-Marie-Tooth Disease (e.g., Charcot-Marie-Tooth type 2A), Optic Atrophy (e.g., autosomal dominant optic atrophy); cardiometabolic diseases such as diabetes, ischemia-reperfusion injury, and cardiomyopathy; cancer (e.g., lung cancer); pulmonary arterial hypertension; patent ductus arteriosus (PDA); acute lung injury; coronary heart disease; and stroke.

In one embodiment, the subject invention provides a method for inhibiting or reducing mitochondrial fission in a subject, the method comprising administering to the subject in need of such inhibition or reduction a compound of the subject invention or a composition of the subject invention.

In specific embodiments, the administration is selected from local, oral, buccal, bronchial, nasal, topical, transdermal, intra-articular, parenteral, or intraspinal administration.

In one embodiment, the subject invention provides a method for preserving/restoring mitochondrial network balance in a cell, the method comprising contacting the cell with a compound of the subject invention or a composition comprising a compound of the subject invention.

In one embodiment, the subject invention provides a method for inhibiting or reducing the activity of Drp1 protein in a cell, the method comprising contacting the cell with a compound of the subject invention or a composition comprising a compound of the subject invention.

In certain embodiments, the cell is from a subject having been diagnosed with a disease associated with, for example, mitochondrial dysfunction, oxidative stress, inflammation and/or autophagy. Preferably, the disease is selected from, for example, Parkinson's disease, Alzheimer's disease, Huntington's disease, ALS, Charcot-Marie-Tooth Disease (e.g., Charcot-Marie-Tooth type 2A), Optic Atrophy (e.g., autosomal dominant optic atrophy), diabetes, ischemia-reperfusion injury, cardiomyopathy, cancer (e.g., lung cancer), pulmonary arterial hypertension, PDA, acute lung injury, coronary heart disease and stroke.

BRIEF DESCRIPTION OF DRAWINGS

FIGS. 2A-2H show that stimulating mitochondrial fission increases mt-ROS generation. Lung EC were transduced with an adenovirus containing human Drp1 (AdDrp1, 2A) to stimulate mitochondrial fission (2B). Drp1 over-expression significantly attenuates mitochondrial bioenergetics using the Seahorse XF24 analyzer (2C-2G). mt-ROS levels from Complex I are also increased (2H). Data are mean±SEM. N=6-10. * P<0.05 vs. control.

FIGS. 5A-5C show the validation of novel Drp1 inhibitors as therapeutics against VILI. Three novel Drp1 inhibitors identified in the Drp1 GTPase assay were tested for their ability to attenuate eNAMPT-mediated mitochondrial fission (5A). One of the compounds CTS2444-32 was further tested in mice exposed to high tidal mechanical ventilation (40 mL/kg, PEEP=5 cm $H_2O$, BR=75 bpm, 4 h). CTS2444-32 (10 mg/kg, i.p., 2 h) decreased lung injury as demonstrated by decreases in total cell counts (5B) and protein (5C) in the bronchoalveolar lavage (BAL) fluid. Values are mean±SEM, n=4. * P<0.05 vs. spontaneously breathing control, †P<0.05 vs. DMSO+VILI.

FIGS. 6A-6I show that Drp1 inhibition attenuates inflammatory cytokine levels in the bronchoalveolar lavage fluid (BALF). CTS2444-32 (10 mg/kg, i.p., 2 h) attenuated the VILI-mediated increase in the levels of TNFα (6A), IL-6 (6B), IL-18 (6C), GROα, (6D), MIP-1α (6E), MIP-1β (6F), MCP-1 (6G), MCP-3 (6H), and IL-12p70 (6I) in the BALF. Values are mean±SEM, n=4. * P<0.05 vs. spontaneously breathing control, †P<0.05 vs. DMSO+VILI.

DETAILED DISCLOSURE

Figure 1A:
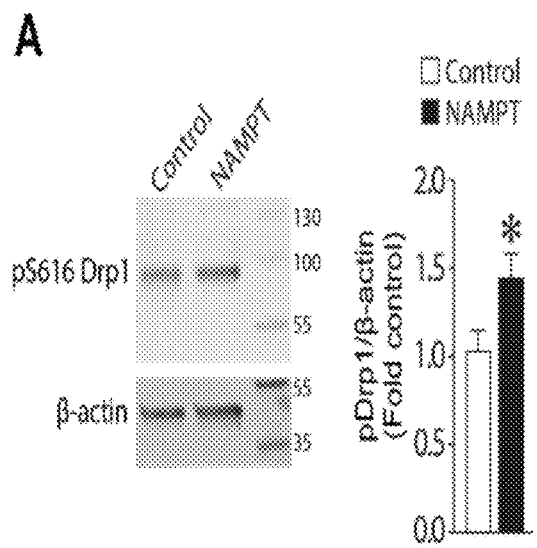
FIGS. 1A-1C show that eNAMPT activates the fission protein, Drp1 in lung EC. eNAMPT treatment (10 μg/ml, 8 h) increases the phosphorylation of Drp1 at S616 (1A). Immunofluorescence imaging shows that eNAMPT also increases the mitochondrial redistribution of Drp1 (1B). TLR4 ligation with LPS (2 EU/ml, 4 h) also increases mitochondrial fission and this is blocked by the putative Drp1 inhibitor, mdivi-1 (1C). Data are mean±SEM. N=3-10. P<0.05 vs. control.

The subject invention provides compounds that specifically inhibit Drp1 protein. The subject invention also provides compositions comprising the compound that inhibits Drp1, and methods for inhibiting Drp1 and treating and/or preventing mitochondrial fission.

In one embodiment, the compounds and compositions of the subject invention can further be used to treat and/or prevent diseases and conditions associated with mitochondrial dysfunction, oxidative stress, inflammation and/or autophagy. The compounds and compositions of the subject invention can also be used to treat a variety of other conditions including, but not limited to, autoimmune disorders, disorders of the nervous system, and cardiovascular disorders.

In one embodiment, the subject invention provides compounds that inhibit Drp1 protein. The exemplary compounds have a structure of:

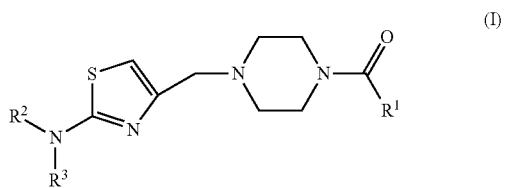

(I)

wherein $R^1$, $R^2$ and $R^3$ are independently selected from, for example, hydrogen, alkyl, substituted alkyl, aryl, substituted aryl, heteroalkyl, substituted heteroalkyl, heteroaryl, substituted heteroaryl, cycloalkyl, substituted cycloalkyl, heterocycloalkyl, substituted heterocycloalkyl, cycloalkenyl, substituted cycloalkenyl, alkenyl, substituted alkenyl, alkynyl, hydroxyl, alkoxyl and hydroxylalkyl.

In one embodiment, $R^1$ is selected from alkyl, substituted alkyl, aryl, substituted aryl, cycloalkyl, and substituted cycloalkyl; and $R^2$ and $R^3$ are independently selected from hydrogen, alkyl, substituted alkyl, aryl, substituted aryl, heteroalkyl, substituted heteroalkyl, heteroaryl, substituted heteroaryl, cycloalkyl, substituted cycloalkyl, heterocycloalkyl, and substituted heterocycloalkyl.

In specific embodiments, $R^1$ is selected from

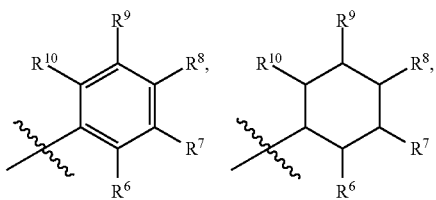

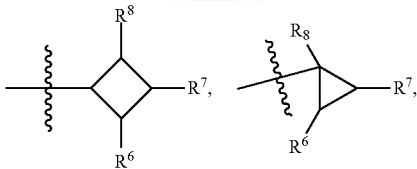

and —CHR$^4$R$^{11}$, wherein, at each occurrence, $R^6$, $R^7$, $R^8$, $R^9$, and $R^{10}$ are independently selected from, for example, hydrogen, halogen, alkyl, substituted alkyl, aryl, substituted aryl, alkoxyl, —OH, —NR$^{13}$R$^{14}$, and acyl; $R^4$ is selected from, for example, hydrogen, alkyl, substituted alkyl, aryl, substituted aryl, heteroalkyl, substituted heteroalkyl, heteroaryl, substituted heteroaryl, cycloalkyl, substituted cycloalkyl, heterocycloalkyl, substituted heterocycloalkyl, cycloalkenyl, substituted cycloalkenyl, alkenyl, substituted alkenyl, alkynyl, hydroxyl, alkoxyl, acyl, alkylamino and hydroxylalkyl; and $R^{11}$ is selected from, for example, hydrogen, halogen, alkyl, substituted alkyl, aryl, substituted aryl, cycloalkyl, and substituted cycloalkyl, alkoxyl, —OH, —NR$^{13}$R$^{14}$, and acyl, wherein, at each occurrence, $R^{13}$ and $R^{14}$ are independently selected from, for example, hydrogen, alkyl, substituted alkyl, aryl, and substituted aryl.

In specific embodiments, $R^2$ and $R^3$ are independently selected from

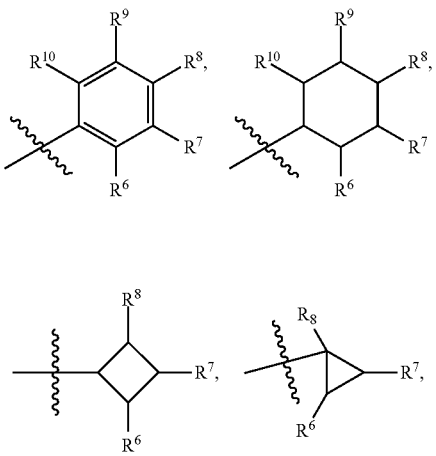

and —CHR$^5$R$^{12}$, wherein, at each occurrence, $R^6$, $R^7$, $R^8$, $R^9$, and $R^{10}$ are independently selected from, for example, hydrogen, halogen, alkyl, substituted alkyl, aryl, substituted aryl, alkoxyl, —OH, —NR$^{13}$R$^{14}$, and acyl; $R^5$ is selected from, for example, hydrogen, alkyl, substituted alkyl, aryl, substituted aryl, heteroalkyl, substituted heteroalkyl, heteroaryl, substituted heteroaryl, cycloalkyl, substituted cycloalkyl, heterocycloalkyl, substituted heterocycloalkyl, cycloalkenyl, substituted cycloalkenyl, alkenyl, substituted alkenyl, hydroxyl, alkynyl, alkoxyl, acyl, alkylamino and hydroxylalkyl; and $R^{12}$ is selected from, for example, hydrogen, halogen, alkyl, substituted alkyl, aryl, substituted aryl, cycloalkyl, and substituted cycloalkyl, alkoxyl, —OH, —NR$^{13}$R$^{14}$, and acyl, wherein, at each occurrence, $R^{13}$ and $R^{14}$ are independently selected from, for example, hydrogen, alkyl, substituted alkyl, aryl, and substituted aryl.

In one embodiment, the compounds that inhibit Drp1 protein have a structure of:

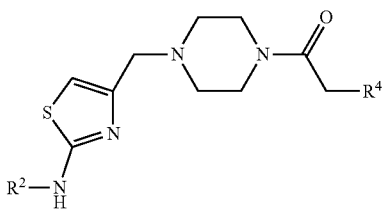

(II)

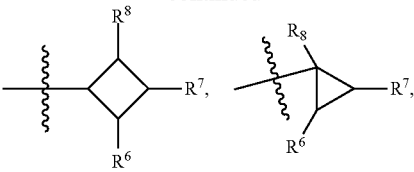

wherein R² is selected from, for example, hydrogen, alkyl, substituted alkyl, aryl, substituted aryl, heteroalkyl, substituted heteroalkyl, heteroaryl, substituted heteroaryl, cycloalkyl, substituted cycloalkyl, heterocycloalkyl, substituted heterocycloalkyl, cycloalkenyl, substituted cycloalkenyl, alkenyl, substituted alkenyl, alkynyl, and hydroxylalkyl; and R⁴ is selected from, for example, hydrogen, alkyl, substituted alkyl, aryl, substituted aryl, heteroalkyl, substituted heteroalkyl, heteroaryl, substituted heteroaryl, cycloalkyl, substituted cycloalkyl, heterocycloalkyl, substituted heterocycloalkyl, cycloalkenyl, substituted cycloalkenyl, alkenyl, substituted alkenyl, alkynyl, hydroxyl, alkoxyl, acyl, alkylamino and hydroxylalkyl.

In one embodiment, the compounds that inhibit Drp1 protein have a structure of:

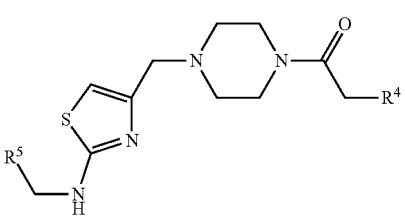

(III)

wherein R⁴ and R⁵ are independently selected from, for example, hydrogen, alkyl, substituted alkyl, aryl, substituted aryl, heteroalkyl, substituted heteroalkyl, heteroaryl, substituted heteroaryl, cycloalkyl, substituted cycloalkyl, heterocycloalkyl, substituted heterocycloalkyl, cycloalkenyl, substituted cycloalkenyl, alkenyl, substituted alkenyl, alkynyl, hydroxyl, alkoxyl, acyl, alkylamino and hydroxylalkyl.

In specific embodiments, R⁴ and R⁵ are independently selected from alkyl, substituted alkyl, aryl, substituted aryl, cycloalkyl, and substituted cycloalkyl.

In specific embodiments, R⁴ and R⁵ are independently selected from

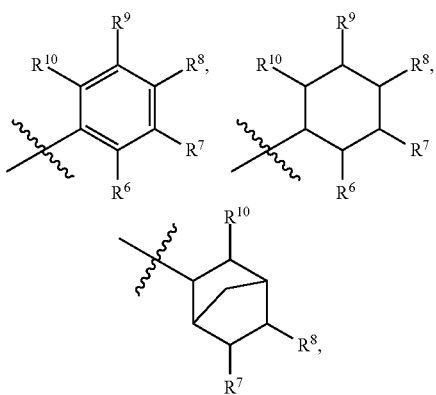

and —CHR¹¹R¹², wherein, at each occurrence, R⁶, R⁷, R⁸, R⁹, and R¹⁰ are independently selected from, for example, hydrogen, halogen, alkyl, substituted alkyl, aryl, substituted aryl, alkoxyl, —OH, —NR¹³R¹⁴, and acyl; and at each occurrence, R¹¹ and R¹² are independently selected from, for example, hydrogen, halogen, alkyl, substituted alkyl, aryl, substituted aryl, cycloalkyl, and substituted cycloalkyl, alkoxyl, —OH, —NR¹³R¹⁴, and acyl, wherein, at each occurrence, R¹³ and R¹⁴ are independently selected from, for example, hydrogen, alkyl, substituted alkyl, aryl, and substituted aryl.

As used herein, "alkyl" means saturated monovalent radicals of at least one carbon atom or a branched saturated monovalent of at least three carbon atoms. It may include straight-chain alkyl groups, branched-chain alkyl groups, and cycloalkyl substituted alkyl groups. It may include hydrocarbon radicals of at least one carbon atom, which may be linear. Examples include, but are not limited to, methyl, ethyl, propyl, 2-propyl, n-butyl, iso-butyl, tert-butyl, pentyl, hexyl, and the like.

As used herein, "acyl" means a radical —C(O)R where R includes, but is not limited to, hydrogen, alkyl, aryl, benzyl, benzoyl, heteroalkyl, heteroaryl, cycloalkyl, heterocycloalkyl, cycloalkenyl, alkenyl, alkynyl, alkoxy, sulfhydryl, halogen, amino, hydroxyl, hydroxylalkyl. Examples include, but are not limited to, formyl, acetyl, ethylcarbonyl, and the like. An acyl group may be substituted or unsubstituted.

As used herein, the terms "alkoxyl" or "alkoxy" refer to an alkyl group, as defined above, having an oxygen radical attached thereto. Examples include, but are not limited to, methoxy, ethoxy, propyloxy, tert-butoxy and the like.

As used herein, "alkylamino" means a radical —NHR or —NR₂ where each R is, independently, an alkyl group. Examples include, but are not limited to, methylamino, (1-methylethyl)amino, dimethyl amino, methylethylamino, di(1-methylethyl)amino, and the like. An alkylamino may be substituted or unsubstituted.

As used herein, "hydroxyalkyl" means an alkyl group substituted with one or more hydroxy groups. Representative examples include, but are not limited to, hydroxymethyl, 2-hydroxyethyl; 2-hydroxypropyl; 3-hydroxypropyl; 1-(hydroxymethyl)-2-methylpropyl; 2-hydroxybutyl; 3-hydroxybutyl; 4-hydroxybutyl; 2,3-dihydroxypropyl; 2-hydroxy-1-hydroxymethylethyl; 2,3-dihydroxybutyl; 3,4-dihydroxybutyl and 2-(hydroxymethyl)-3-hydroxy-propyl; preferably 2-hydroxyethyl; 2,3-dihydroxypropyl and 1-(hydroxymethyl) 2-hydroxyethyl. A hydroxyalkyl may be substituted or unsubstituted.

As used herein, "alkenyl" refers to a straight or branched hydrocarbon chain containing one or more double bonds. Although the present definition covers the occurrence of the term "alkenyl" where no numerical range is designated, the alkenyl group may have at least 2, 3, 4, 5, 6, 7, 8, 9, 10, 11, 12, 13, 14, 15, 16, 17, 18, 19, or 20 carbon atoms, or any number in between. For example, the alkenyl group may be designated as "$C_{2-4}$ alkenyl," "$C_{2-10}$ alkenyl," "$C_{2-20}$ alkenyl" or similar designations. By way of example only, "$C_{2-4}$ alkenyl" indicates that there are two to four carbon atoms in the alkenyl chain, i.e., the alkenyl chain is selected from ethenyl; propen-1-yl; propen-2-yl; propen-3-yl; buten-1-yl; buten-2-yl; buten-3-yl; buten-4-yl; 1-methyl-propen-1-yl; 2-methyl-propen-1-yl; 1-ethyl-ethen-1-yl; 2-methyl-propen-3-yl; buta-1,3-dienyl; buta-1,2-dienyl and buta-1,2-dien-4-yl. Typical alkenyl groups include, but are in no way limited to, ethenyl, propenyl, butenyl, pentenyl, and hexenyl, and the like.

As used herein, "alkynyl" refers to a straight or branched hydrocarbon chain comprising one or more triple bonds. Although the present definition covers the occurrence of the term "alkynyl" where no numerical range is designated, the alkynyl group may have at least 2, 3, 4, 5, 6, 7, 8, 9, 10, 11, 12, 13, 14, 15, 16, 17, 18, 19, or 20 carbon atoms, or any number in between. For example, the alkynyl group may be designated as "$C_{2-4}$ alkynyl" "$C_{2-10}$ alkynyl" "$C_{2-20}$ alkynyl" or similar designations. By way of example only, "$C_{2-4}$ alkynyl" indicates that there are two to four carbon atoms in the alkynyl chain, e.g., the alkynyl chain is selected from ethynyl, propyn-1-yl, propyn-2-yl, butyn-1-yl, butyn-3-yl, butyn-4-yl, and 2-butynyl. Typical alkynyl groups include, but are in no way limited to, ethynyl, propynyl, butynyl, pentynyl, and hexynyl, and the like.

As used herein, "cycloalkyl" means a fully saturated carbocyclic ring radical or ring system. Examples include, but are not limited to, cyclopropyl, cyclobutyl, cyclopentyl, and cyclohexyl.

As used herein, "aryl" refers to a carbocyclic (all carbon) monocyclic or multicyclic aromatic ring system (including fused ring systems where two carbocyclic rings share a chemical bond). The number of carbon atoms in an aryl group can vary. For example, the aryl group can be a $C_6$-$C_{14}$ aryl group, a $C_6$-$C_{10}$ aryl group, or a $C_6$ aryl group. Examples of aryl groups include, but are not limited to, phenyl, benzyl, α-naphthyl, ß-naphthyl, biphenyl, anthryl, tetrahydronaphthyl, fluorenyl, indanyl, biphenylenyl, and acenaphthenyl. Preferred aryl groups are phenyl and naphthyl.

As used herein, "heteroaryl" refers to an aromatic ring or ring system (i.e., two or more fused rings that share two adjacent atoms) that comprise(s) one or more heteroatoms, that is, an element other than carbon, including but not limited to, nitrogen, oxygen and sulfur, in the ring backbone. When the heteroaryl is a ring system, every ring in the system is aromatic. The heteroaryl group may have 5-18 ring members (i.e., the number of atoms making up the ring backbone, including carbon atoms and heteroatoms), although the present definition also covers the occurrence of the term "heteroaryl" where no numerical range is designated. Examples of heteroaryl rings include, but are not limited to, furyl, thienyl, phthalazinyl, pyrrolyl, oxazolyl, thiazolyl, imidazolyl, pyrazolyl, isoxazolyl, isothiazolyl, triazolyl, thiadiazolyl, pyridinyl, pyridazinyl, pyrimidinyl, pyrazinyl, triazinyl, quinolinyl, isoquinlinyl, benzimidazolyl, benzoxazolyl, benzothiazolyl, indolyl, isoindolyl, and benzothienyl.

As used herein, a "substituted" group may be substituted with one or more group(s) individually and independently selected from alkyl, alkenyl, alkynyl, cycloalkyl, cycloalkenyl, cycloalkynyl, benzyl, substituted benzyl, aryl, heteroaryl, heteroalicyclyl, aralkyl, heteroaralkyl, (heteroalicyclyl)alkyl, hydroxyl, protected hydroxyl, alkoxyl, aryloxy, acyl, mercapto, alkylthio, arylthio, cyano, halogen, thiol, thiocarbonyl, O-carbamyl, N-carbamyl, O-thiocarbamyl, N-thiocarbamyl, C-amido, N-amido, S-sulfonamido, N-sulfonamido, C-carboxy, protected C-carboxy, O-carboxy, isocyanato, thiocyanato, isothiocyanato, nitro, silyl, sulfenyl, sulfinyl, sulfonyl, haloalkyl, haloalkoxy, trihalomethanesulfonyl, trihalomethanesulfonamido, an amino, a mono-substituted amino group and a di-substituted amino group, and protected derivatives thereof.

As used herein, "halogen" refers to an atom of fluorine, chlorine, bromine or iodine.

In a specific embodiment, the compounds that inhibit Drp1 protein are selected from

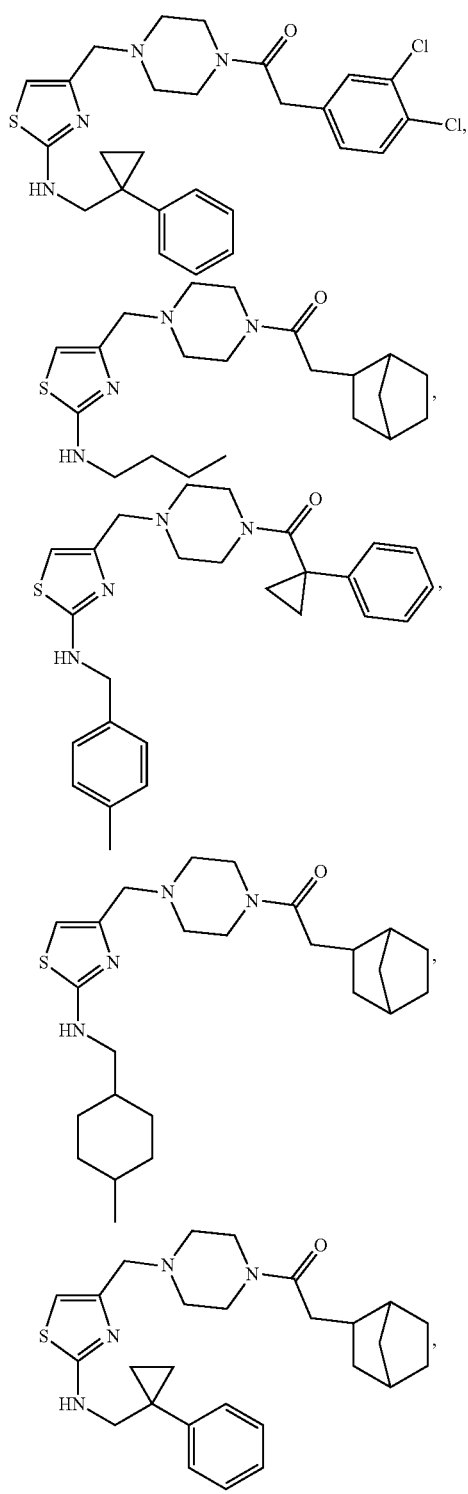

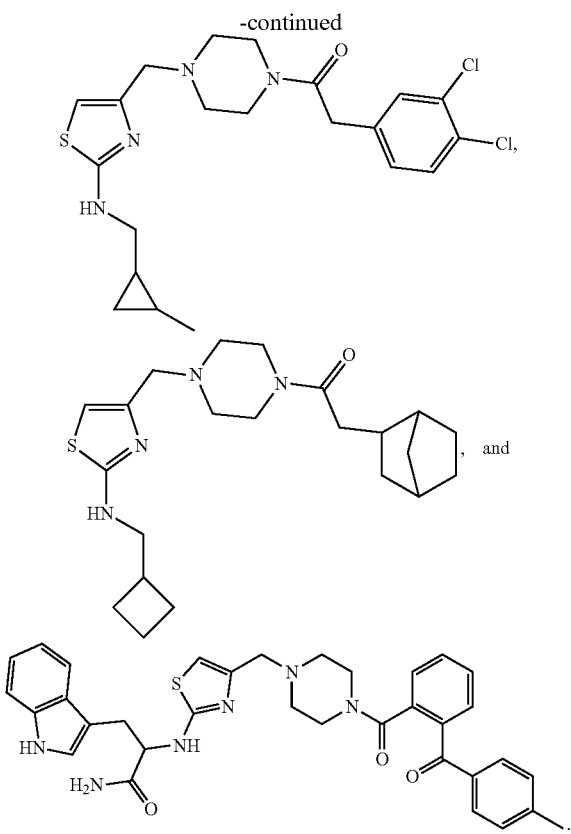

In one embodiment, the subject invention provides a composition comprising a compound of the subject invention, or a pharmaceutically acceptable salt thereof. In certain embodiments, the subject invention provides a pharmaceutical composition comprising a Drp1 inhibitor, or a pharmaceutically acceptable salt thereof. Pharmaceutically acceptable salt as used herein includes, for example, salts that have the desired pharmacological activity of the parent compound (salts which retain the biological effectiveness and/or properties of the parent compound and which are not biologically and/or otherwise undesirable). The acid salts can be generated with any pharmaceutically acceptable organic or inorganic acid.

Pharmaceutically acceptable salts may be derived from, for example, and without limitation, acetic acid, adipic acid, alginic acid, aspartic acid, ascorbic acid, benzoic acid, benzenesulfonic acid, butyric acid, cinnamic acid, citric acid, camphoric acid, camphorsulfonic acid, cyclopentanepropionic acid, diethylacetic acid, digluconic acid, dodecylsulfonic acid, ethanesulfonic acid, formic acid, fumaric acid, glucoheptanoic acid, gluconic acid, glycerophosphoric acid, glycolic acid, hemisulfonic acid, heptanoic acid, hexanoic acid, hydrochloric acid, hydrobromic acid, hydriodic acid, 2-hydroxyethanesulfonic acid, isonicotinic acid, lactic acid, malic acid, maleic acid, malonic acid, mandelic acid, methanesulfonic acid, 2-napthalenesulfonic acid, naphthalenedisulphonic acid, p-toluenesulfonic acid, nicotinic acid, nitric acid, oxalic acid, pamoic acid, pectinic acid, 3-phenylpropionic acid, phosphoric acid, picric acid, pimelic acid, pivalic acid, propionic acid, pyruvic acid, salicylic acid, succinic acid, sulfuric acid, sulfamic acid, tartaric acid, thiocyanic acid or undecanoic acid. Salts, as described herein, may be prepared by conventional processes known to a person skilled in the art, for example, and without limitation, by combining the free form with an organic acid or cation exchange from other salts. Those skilled in the art will appreciate that preparation of salts may occur in situ during isolation and purification of the compounds or preparation of salts may occur by separately reacting an isolated and purified compound.

In some embodiments, the compounds may be in the form of a solvate. Solvates contain either stoichiometric or non-stoichiometric amounts of a solvent in physical association the compound or salt thereof. The solvent may be, for example, and without limitation, a pharmaceutically acceptable solvent. For example, hydrates are formed when the solvent is water or alcoholates are formed when the solvent is an alcohol.

In one embodiment, the composition according to the subject invention also comprises a pharmaceutically acceptable carrier. "Pharmaceutically acceptable carrier" refers to a diluent, adjuvant or excipient with which the one or more active agents disclosed herein can be formulated. Typically, a "pharmaceutically acceptable carrier" is a substance that is non-toxic, biologically tolerable, and otherwise biologically suitable for administration to a subject, such as an inert substance, added to a pharmacological composition or otherwise used as a diluent, adjuvant or excipient to facilitate administration of the composition disclosed herein and that is compatible therewith.

Examples of carriers suitable for use in the pharmaceutical compositions are known in the art and such embodiments are within the purview of the subject invention. The pharmaceutically acceptable carriers and excipients include, but not limited to, aqueous vehicles, water-miscible vehicles, non-aqueous vehicles, stabilizers, solubility enhancers, isotonic agents, buffering agents, suspending and dispersing agents, wetting or emulsifying agents, complexing agents, sequestering or chelating agents, cryoprotectants, lyoprotectants, thickening agents, pH adjusting agents, and inert gases. Other suitable excipients or carriers include, but are not limited to, dextran, glucose, maltose, sorbitol, xylitol, fructose, sucrose, and trehalose.

In one embodiment, the pharmaceutical composition comprising compounds according to the invention, together with a conventional adjuvant, carrier, or diluent, may be placed into the form of solids including tablets, filled capsules, powder and pellet forms, and liquids such as aqueous or non-aqueous solutions, suspensions, emulsions, elixirs, and capsules filled with the same. The composition may further comprise conventional ingredients in conventional proportions, with or without additional active compounds. In one embodiment, the composition may be formulated for administration as tablets, coated tablets, nasal sprays, solutions, emulsions, liposomes, powders, capsules or sustained release forms.

The compositions of the present invention can be administered to the subject being treated by standard routes, including the local, oral, buccal, bronchial, ophthalmic, sub-lingual, nasal, topical, intratumoural, transdermal, intra-articular, parenteral (e.g., intravenous, intraperitoneal, intradermal, subcutaneous or intramuscular), intracranial, intracerebral, intraspinal, intravaginal, intrauterine, or rectal route. Administration may be also by way of other carriers or vehicles such as patches, micelles, liposomes, vesicles, implants (e.g., microimplants), synthetic polymers, microspheres, nanoparticles, and the like. Depending on the condition being treated, one route may be preferred over others, which can be determined by those skilled in the art.

In one embodiment, the composition can be applied directly to the nasal cavity by conventional means, for example with a dropper, pipette or spray. The compositions may be provided in single or multi-dose form. Drops may be formulated with an aqueous or non-aqueous base also comprising one or more dispersing agents, solubilizing agents, or suspending agents. Administration to the respiratory tract may also be achieved by means of an aerosol formulation in which the active ingredient is provided in a pressurized pack with a suitable propellant such as a chlorofluorocarbon (CFC) for example dichlorodifluoromethane, trichlorofluoromethane, or dichlorotetrafluoroethane, carbon dioxide, or other suitable gas. Aerosol dosages can be controlled by providing a valve to deliver a metered amount of the compound or a pharmaceutically acceptable salt thereof.

In one embodiment, the composition can be formulated in solutions or suspensions for parenteral, intradermal, or subcutaneous application, which can include the following components: a sterile diluent such as water for injection, saline solution, fixed oils, polyethylene glycols, glycerine; propylene glycol or other synthetic solvents; antibacterial agents such as benzyl alcohol or methyl parabens; antioxidants such as ascorbic acid or sodium bisulfate; chelating agents such as ethylenediaminetetraacetic acid; buffers such as acetates, citrates or phosphates and agents for the adjustment of tonicity such as sodium chloride or dextrose. pH can be adjusted with acids or bases, such as hydrochloric acid or sodium hydroxide. The parenteral preparation can be enclosed in ampoules, disposable syringes or multiple dose vials made of glass or plastic.

Pharmaceutical compositions suitable for injectable use include sterile aqueous solutions (where water soluble) or dispersions and sterile powders for the extemporaneous preparation of sterile injectable solutions or dispersion. For intravenous administration, suitable carriers include physiological saline, bacteriostatic water, Cremophor EL™ (BASF, Parsippany, N.J.) or phosphate buffered saline (PBS). In all cases, the injectable composition should be sterile and should be fluid to the extent that easy syringability exists. It must be stable under the conditions of manufacture and storage and must be preserved against the contaminating action of microorganisms such as bacteria and fungi. The proper fluidity can be maintained, for example, by the use of a coating such as lecithin, by the maintenance of the required particle size in the case of dispersion and by the use of surfactants. Prevention of the action of microorganisms can be achieved by various antibacterial and antifungal agents, for example, parabens, chlorobutanol, phenol, ascorbic acid, thimerosal, and the like. In many cases, it will be preferable to include isotonic agents, for example, sugars, polyalcohols such as manitol, sorbitol, and sodium chloride in the composition. Prolonged absorption of the injectable compositions can be brought about by including in the composition an agent which delays absorption, for example, aluminium monostearate and gelatin. In the case of sterile powders for the preparation of sterile injectable solutions, the preferred methods of preparation are, for example, vacuum drying and freeze-drying techniques.

In one embodiment, the composition may be formulated in an aqueous solution for oral administration. The composition may be dissolved in suitable solutions with added suitable colorants, flavors, stabilizing and thickening agents, artificial and natural sweeteners, and the like. In addition, the composition may further be dissolved in solution containing viscous material, such as natural or synthetic gums, resins, methylcellulose, sodium carboxymethylcellulose, or other well-known suspending agents.

Oral compositions may include an inert diluent or an edible carrier. They can be enclosed in gelatin capsules or compressed into tablets. For the purpose of oral therapeutic administration, the active compound can be incorporated with excipients and used in the form of tablets, troches, or capsules. Pharmaceutically compatible binding agents, and/or adjuvant materials can be included as part of the composition. The tablets, pills, capsules, troches and the like can contain any of the following ingredients, or compounds of a similar nature: a binder (such as microcrystalline cellulose, gelatin, a sugar, polyethylene glycol, natural and synthetic gums, polyvinylpyrrolidone, pregelatinised starch, hydroxypropyl cellulose and hydroxypropyl methylcellulose); an excipient (such as such as lactose, mannitol, xylitol, dextrose, sucrose, sorbitol, microcrystalline cellulose, starch, and dibasic calcium phosphate dehydrate); a disintegrating agent (such as alginic acid, Primogel, sodium starch glycolate, sodium carboxymethyl cellulose, calcium carboxymethyl cellulose, polyvinylpyrrolidone, methyl cellulose, microcrystalline cellulose, lower alkyl-substituted hydroxypropyl cellulose, starch, pregelatinised starch and sodium alginate); a lubricant (such as magnesium stearate, calcium stearate, zinc stearate, sodium stearyl fumarate, and mixtures of magnesium stearate with sodium lauryl sulfate); a glidant such as colloidal silicon dioxide; a sweetening agent such as sucrose or saccharin; or a flavoring agent such as peppermint, methyl salicylate, or orange flavoring.

In one embodiment, the composition can be administered by inhalation. For example, the compounds are delivered in the form of an aerosol spray from pressured container or dispenser which contains a suitable propellant, e.g., a gas such as carbon dioxide, or a nebulizer. Pharmaceutical compositions for administration by inhalation or insufflation may also be provided in the form of a dry powder composition, and a suitable powder base such as lactose or starch. Such powder composition can be provided in unit dosage form, for example, in capsules, cartridges, gelatin packs, or blister packs, from which the powder can be administered with the aid of an inhalator or insufflator.

The composition of the subjection invention may also be administered in a controlled release formulation such as a slow release or a fast release formulation. Such controlled release formulations of the combinations of this invention may be prepared using methods well known to those skilled in the art. The method of administration will be determined by the attendant physician or other person skilled in the art after an evaluation of the subject's condition and requirements.

In one embodiment, the pharmaceutical composition is provided in a unit dosage form, wherein the composition in desired form is divided into unit doses containing appropriate quantities of the active component. The unit dosage form can be a packaged preparation, the package containing discrete quantities such as packaged tablets, capsules, and powders in vials or ampoules. Moreover, the unit dosage form can be a capsule, tablet, cachet, or lozenge itself, or it can be the appropriate number of any of these in packaged form. In a preferred embodiment, tablet or capsule forms are for oral administration and liquid form are for intravenous administration and continuous infusion.

In one embodiment, dosage units containing the drug contain about 0.01 mg to 1000 mg, about 0.01 mg to 900 mg, about 0.01 mg to 800 mg, about 0.01 mg to 700 mg, about 0.01 mg to 600 mg, about 0.01 mg to 500 mg, about 0.05 mg to 500 mg, about 0.1 mg to 400 mg, about 0.1 mg to 300 mg, about 0.1 mg to 200 mg, about 0.1 mg to 100 mg, about 0.1 mg to 90 mg, about 0.1 mg to 80 mg, about 0.1 mg to 70 mg, about 0.1 mg to 60 mg, about 0.1 mg to 50 mg, about 0.1 mg to 40 mg, about 0.1 mg to 30 mg, about 0.1 mg to 20 mg, about 0.1 mg to 10 mg, about 0.5 mg to 50 mg, about 1 mg to 40 mg, about 1 mg to 20 mg, about 1 mg to 10 mg, or about 1 mg to 5 mg.

In one embodiment, the subject invention further provides a method for treating and/or preventing a disease or condition by using the Drp1 inhibitor of the subject invention. In one embodiment, the method comprises administering to a subject in need of such treatment a compound of the subject invention or a composition of the subject invention comprising the compound of the subject invention.

In one embodiment, the method of the subjection involves the inhibition of Drp1 protein and/or mitochondrial fission. Thus, the method may further comprise a step of determining the activity of Drp1 from a sample obtained from the subject.

The term "subject" or "patient," as used herein, describes an organism, including mammals such as primates, to which diagnosis, prevention, assessment, and/or treatment according to the present invention can be provided. Mammalian species that can benefit from the disclosed methods of treatment include, but are not limited to, apes, chimpanzees, orangutans, humans, and monkeys; domesticated animals such as dogs, cats; live stocks such as horses, cattle, pigs, sheep, goats, and chickens; and other animals such as mice, rats, guinea pigs, and hamsters.

The terms "treatment" or any grammatical variation thereof (e.g., treat, treating, etc.), as used herein, includes but is not limited to, the application or administration to a subject (or application or administration to a cell or tissue from a subject) with the purpose of delaying, slowing, stabilizing, curing, healing, alleviating, relieving, altering, remedying, less worsening, ameliorating, improving, or affecting the disease or condition, the symptom of the disease or condition, or the risk of (or susceptibility to) the disease or condition. The term "treating" refers to any indication of success in the treatment or amelioration of a pathology or condition, including any objective or subjective parameter such as abatement; remission; lessening of the rate of worsening; lessening severity of the disease; stabilization, diminishing of symptoms or making the pathology or condition more tolerable to the subject; or improving a subject's physical or mental well-being.

In certain embodiments, the diseases or conditions are associated with mitochondrial dysfunction, oxidative stress, inflammation and/or autophagy. Preferably, the diseases or conditions are associated with mitochondrial fission. For example, the diseases or conditions include, but are not limited to, neurodegenerative diseases such as Parkinson's disease, Alzheimer's disease, Huntington's disease and amyotrophic lateral sclerosis (ALS); neuropathies such as Charcot-Marie-Tooth Disease (e.g., Charcot-Marie-Tooth type 2A), Optic Atrophy (e.g., autosomal dominant optic atrophy); cardiometabolic diseases such as diabetes, ischemia-reperfusion injury, and cardiomyopathy; cancer (e.g., lung cancer); pulmonary arterial hypertension; patent ductus arteriosus (PDA); acute lung injury; coronary heart disease; and stroke.

In one embodiment, the subject invention further provides methods for treating a cancer/tumor, the method comprising administering, to a subject in need of such treatment, an effective amount of the compound of the subject invention or the therapeutic formulation/composition of the subject invention.

In certain embodiments, the compounds and compositions of the subject invention provides treatment for cancers including, but not limited to, carcinoma, lymphoma, blastoma, sarcoma, and leukemia or lymphoid malignancies. More particular examples of such cancers include squamous cell cancer (e.g. epithelial squamous cell cancer), lung cancer including small-cell lung cancer, non-small cell lung cancer, adenocarcinoma of the lung and squamous carcinoma of the lung, cancer of the peritoneum, hepatocellular cancer, gastric or stomach cancer including gastrointestinal cancer, pancreatic cancer, glioblastoma, cervical cancer, ovarian cancer, oral cancer, liver cancer, bladder cancer, cancer of the urinary tract, hepatoma, breast cancer including, for example, HER2-positive breast cancer, colon cancer, rectal myeloma and B-cell lymphoma, brain cancer, head and neck cancers, and associated metastases.

In one embodiment, the subject invention further provides methods for treating acute lung injury, the method comprising administering, to a subject in need of such treatment, an effective amount of the compound of the subject invention or the therapeutic formulation/composition of the subject invention.

In one embodiment, the subject invention further provides methods for treating acute respiratory distress syndrome (ARDS), the method comprising administering, to a subject in need of such treatment, an effective amount of the compound of the subject invention or the therapeutic formulation/composition of the subject invention.

In one embodiment, the subject invention further provides methods for treating Parkinson's disease, the method comprising administering, to a subject in need of such treatment, an effective amount of the compound of the subject invention or the therapeutic formulation/composition of the subject invention.

In one embodiment, the subject invention further provides methods for inhibiting or reducing mitochondrial fission in a subject, the method comprising administering to the subject an effective amount of the compound of the subject invention or the therapeutic formulation/composition of the subject invention.

In some embodiments, the Drp1 inhibitor of the subject invention can inhibit/reduce mitochondrial fission/mitochondrial fragmentation in the subject, preferably, under pathological conditions. For example, the Drp1 inhibitor of the subject invention can inhibit/reduce mitochondrial fission/mitochondrial fragmentation by at least about 10%, at least about 15%, at least about 20%, at least about 25%, at least about 30%, at least about 35%, at least about 40%, at least about 45%, at least about 50%, at least about 55%, at least about 60%, at least about 65%, at least about 70%, at least about 75%, at least about 80%, at least about 85%, at least about 90%, at least about 95%, or more than 95%, compared to the degree of mitochondrial fission/mitochondrial fragmentation in the absence of the Drp1 inhibitor.

In one embodiment, the subject invention further provides methods for preserving/restoring mitochondrial network balance in a subject, the method comprising administering to the subject an effective amount of the compound of the subject invention or the therapeutic formulation/composition of the subject invention.

In some embodiments, the Drp1 inhibitor of the subject invention can restore mitochondrial network balance in the subject by at least about 10%, at least about 15%, at least about 20%, at least about 25%, at least about 30%, at least about 35%, at least about 40%, at least about 45%, at least about 50%, at least about 55%, at least about 60%, at least about 65%, at least about 70%, at least about 75%, at least about 80%, at least about 85%, at least about 90%, at least about 95%, or more than 95%, compared to the degree of the disrupted mitochondrial network balance in the absence of the Drp1 inhibitor.

In one embodiment, the subject invention provides a method for inhibiting or reducing the activity of Drp1 protein in a subject, the method comprising administering to the subject an effective amount of the compound of the subject invention or the therapeutic formulation/composition of the subject invention.

In some embodiments, the Drp1 inhibitor of the subject invention can inhibit/reduce GTPase activity of Drp1 in the subject by at least about 10%, at least about 15%, at least about 20%, at least about 25%, at least about 30%, at least about 35%, at least about 40%, at least about 45%, at least about 50%, at least about 55%, at least about 60%, at least about 65%, at least about 70%, at least about 75%, at least about 80%, at least about 85%, at least about 90%, at least about 95%, or more than 95%, compared to the level of GTPase activity of Drp1 in the absence of the inhibitor.

The compositions can be administered to a subject by methods including, but not limited to, (i) administration through oral pathways, which administration includes administration in capsule, tablet, granule, spray, syrup, or other such forms; (ii) administration through non-oral pathways, which administration includes administration as an aqueous suspension, an oily preparation or the like or as a drip, suppository, salve, ointment or the like; administration via injection, subcutaneously, intraperitoneally, intravenously, intramuscularly, intradermally, or the like; as well as (iii) administration topically, or as deemed appropriate by those of skill in the art for bringing the compound into contact with living tissue; and (iv) administration via controlled released formulations, depot formulations, and infusion pump delivery.

An "effective amount" of a pharmaceutical composition includes a therapeutically effective amount or a prophylactically effective amount. A "therapeutically effective amount" refers to an amount effective, at dosages and for periods of time necessary, to achieve the desired therapeutic result. A therapeutically effective amount of a formulation may vary according to factors such as the disease state, age, sex, and weight of the subject, and the ability of the compound to elicit a desired response in the subject. Dosage regimens may be adjusted to provide the optimum therapeutic response. A therapeutically effective amount is also one in which any toxic or detrimental effects of the compound are outweighed by the therapeutically beneficial effects. A "prophylactically effective amount" refers to an amount effective, at dosages and for periods of time necessary, to achieve the desired prophylactic result. Typically, a prophylactic dose is used in subjects prior to a condition or disease, so that a prophylactically effective amount may be less than a therapeutically effective amount.

In specific embodiments, the composition of the subject invention may be administered at least once a day, twice a day, or three times a day for consecutive days, e.g., 2, 3, 4, 5, 6, 7, 8, 9, 10, 11, 12, 13, 14, 15, 16, 17, 18, 19, 20, 21, 22, 23, 24, 25, 26, 27, 28, 29, or 30 days. The composition of the subject invention may also be administered for weeks, months or years.

Dosage values may vary with the severity of the condition to be alleviated. For any particular subject, specific dosage regimens may be adjusted over time according to the individual need and the professional judgment of the person administering or supervising the administration of the compositions. Dosage ranges suggested herein are exemplary only and do not limit the dosage ranges that may be selected by medical practitioners. The amount of the mercaptan based compounds and derivatives in the composition may vary according to factors such as the disease state, age, sex, and weight of the subject. Dosage regimens may be adjusted to provide the optimum therapeutic response.

In one embodiment, the subject invention further provides methods for preserving/restoring mitochondrial network balance in a cell, the method comprising contacting the cell with a compound of the subject invention or a composition of the subjection invention comprising the compound of the subject invention.

In some embodiments, the Drp1 inhibitor of the subject invention can restore mitochondrial network balance in a cell by at least about 10%, at least about 15%, at least about 20%, at least about 25%, at least about 30%, at least about 35%, at least about 40%, at least about 45%, at least about 50%, at least about 55%, at least about 60%, at least about 65%, at least about 70%, at least about 75%, at least about 80%, at least about 85%, at least about 90%, at least about 95%, or more than 95%, compared to the degree of the disrupted mitochondrial network balance in the absence of the Drp1 inhibitor.

In one embodiment, the subject invention provides a method for inhibiting or reducing mitochondrial fission in a cell, the method comprising contacting the cell with a compound of the subject invention or a composition of the subjection invention comprising the compound of the subject invention.

In some embodiments, the Drp1 inhibitor of the subject invention can inhibit/reduce mitochondrial fission/mitochondrial fragmentation in a cell, preferably, under pathological conditions (e.g., where mitochondria in the cell are undergoing pathological mitochondrial fission). For example, the Drp1 inhibitor of the subject invention can inhibit/reduce mitochondrial fission/mitochondrial fragmentation in a cell by at least about 10%, at least about 15%, at least about 20%, at least about 25%, at least about 30%, at least about 35%, at least about 40%, at least about 45%, at least about 50%, at least about 55%, at least about 60%, at least about 65%, at least about 70%, at least about 75%, at least about 80%, at least about 85%, at least about 90%, at least about 95%, or more than 95%, compared to the degree of mitochondrial fission/mitochondrial fragmentation in the absence of the Drp1 inhibitor.

In one embodiment, the subject invention provides a method for inhibiting or reducing the activity of Drp1 protein in a cell, the method comprising contacting the cell with a compound of the subject invention or a composition of the subjection invention comprising the compound of the subject invention.

In one embodiment, the method may further comprise a step of determining the activity of Drp1 in the cell. Preferably, the cell is obtained from a subject. In specific embodiments, the subject has been diagnosed with a disease or condition associated with, for example, mitochondrial dysfunction, oxidative stress, inflammation and/or autophagy.

In some embodiments, the Drp1 inhibitor of the subject invention can inhibit/reduce GTPase activity of Drp1 in a cell by at least about 10%, at least about 15%, at least about 20%, at least about 25%, at least about 30%, at least about 35%, at least about 40%, at least about 45%, at least about 50%, at least about 55%, at least about 60%, at least about 65%, at least about 70%, at least about 75%, at least about 80%, at least about 85%, at least about 90%, at least about 95%, or more than 95%, compared to the level of GTPase activity of Drp1 in the absence of the inhibitor.

In some embodiments, contacting the cell with the compound of the subject invention may comprise incubating the cell with the compound of the subject invention or intracellularly delivery of the compound of the subject invention.

As used herein, the singular forms "a," "an," and "the" are intended to include the plural forms as well, unless the context clearly indicates otherwise. Further, to the extent that the terms "including," "includes," "having," "has," "with," or variants thereof are used in either the detailed description and/or the claims, such terms are intended to be inclusive in a manner similar to the term "comprising." The transitional terms/phrases (and any grammatical variations thereof), such as "comprising," "comprises," and "comprise," can be used interchangeably. The transitional term "comprising," "comprises," or "comprise" is inclusive or open-ended and does not exclude additional, unrecited elements or method steps. By contrast, the transitional phrase "consisting of" excludes any element, step, or ingredient not specified in the claim. The phrases "consisting of" or "consists essentially of" indicate that the claim encompasses embodiments containing the specified materials or steps and those that do not materially affect the basic and novel characteristic(s) of the claim. Use of the term "comprising" contemplates other embodiments that "consist of" or "consisting essentially of" the recited component(s).

The term "about" or "approximately" means within an acceptable error range for the particular value as determined by one of ordinary skill in the art, which will depend in part on how the value is measured or determined, i.e., the limitations of the measurement system. For example, "about" can mean within 1 or more than 1 standard deviation, per the practice in the art. Alternatively, "about" can mean a range of up to 0-20%, 0 to 10%, 0 to 5%, or up to 1% of a given value. Alternatively, particularly with respect to biological systems or processes, the term can mean within an order of magnitude, preferably within 5-fold, and more preferably within 2-fold, of a value. Where particular values are described in the application and claims, unless otherwise stated the term "about" meaning within an acceptable error range for the particular value should be assumed. In the context of compositions containing amounts of concentrations of ingredients where the term "about" is used, these values include a variation (error range) of 0-10% around the value (X±10%).

The recitation of a listing of chemical groups in any definition of a variable herein includes definitions of that variable as any single group or combination of listed groups. The recitation of an embodiment for a variable or aspect herein includes that embodiment as any single embodiment or in combination with any other embodiments or portions thereof.

When ranges are used herein, such as for dose ranges, combinations and subcombinations of ranges (e.g., subranges within the disclosed range), specific embodiments therein are intended to be explicitly included.

EXAMPLES

Example 1—Drp1 as a Therapeutic Target for VILI/ARDS

Mitochondrial networks are dynamic, constantly forming elongated tubes through fusion and splitting into small, less connected mitochondria through fission. Optimizing this "mitochondrial network remodeling" is critical for mitochondrial homeostasis. Fusion permits the mixing of the contents between mitochondria and maybe a pathway that protects the mitochondria. Three mitochondrial guanosine triphosphatases (GTPases) regulate mitochondrial fusion: the mitofusins (Mfn)-1 & -2 and the optic atrophy 1 protein (OPA-1).

Fission is mediated through the GTPase activity of dynamin-related protein1 (Drp1, DNM1L). Drp1 is present in the cytosol and translocates to the mitochondria when activated. On the mitochondrion, it assembles into oligomeric structures that mechanically constrict and fragment the mitochondria. The activity of Drp1 is predominantly regulated by post-translational modifications (PTMs). Phosphorylation of Drp1 is the most studied PTM. Phosphorylation of a C-terminal serine residue at Ser616 activates Drp1 promoting mitochondrial fission and mitochondria fragmentation. Several kinases can phosphorylate Drp1 at Ser616, including Rho kinase (ROCK).

Mechanical ventilation directly contributes to de novo lung injury and exaggerates established acute lung injury, a condition known as ventilator-induced lung injury (VILI), leading to acute respiratory distress syndrome (ARDS). VILI shares pathobiological features with ARDS, including marked lung endothelial cell (EC) barrier disruption, inflammation, and pulmonary edema. The expression and release of the ARDS biomarker, extracellular nicotinamide phosphoribosyltransferase (eNAMPT), is increased by mechanical stress. In VILI/ARDS, the ligation of Toll-like receptor 4 (TLR4) on endothelial cells (EC) triggers an inflammatory response. This includes increased generation of pro-inflammatory cytokines and chemokines, reactive oxygen (ROS) and nitrogen (RNS) species, the disruption of the EC barrier, and the activation, recruitment, and infiltration of immune cells.

Figure 1B:
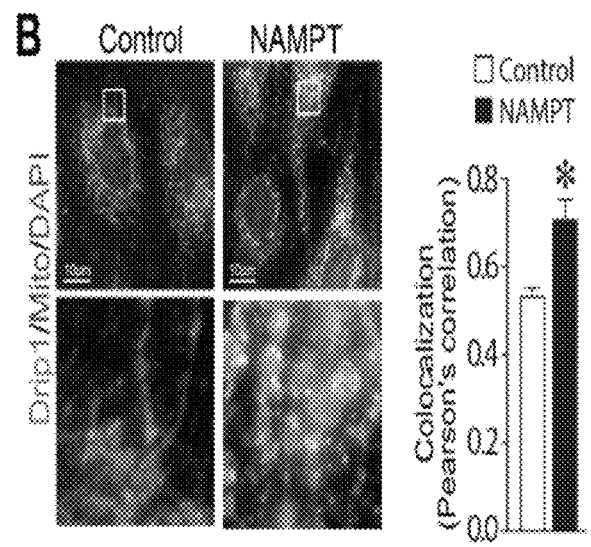
Figure 1C:
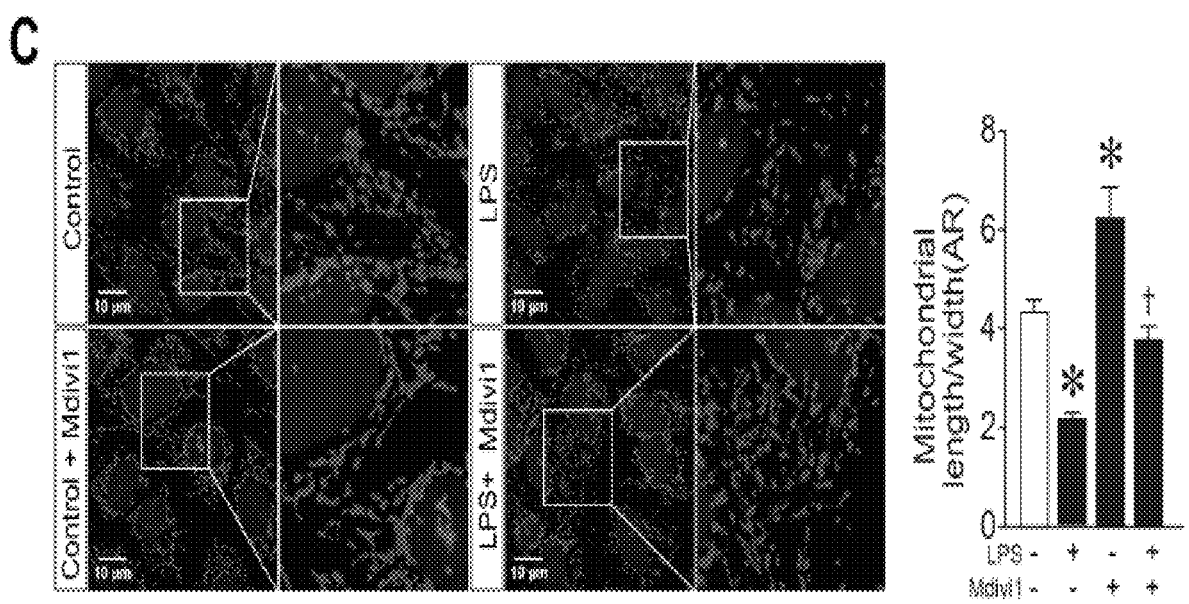

The result shows that eNAMPT, a damage-associated molecular pattern (DAMP) molecule and a novel innate immunity modulator of TLR4-mediated pro-inflammatory responses increases pS616-Drp1 levels (FIG. 1A). pS616-Drp1 is associated with the redistribution of Drp1 to the mitochondria. Using immunofluorescence microscopy, increased mitochondrial localization of Drp1 was observed (FIG. 1B). The putative Drp1 inhibitor, mdivi-1, decreases TLR4-dependent mitochondrial fission (FIG. 1C), confirming the role of Drp1.

Figure 2H:
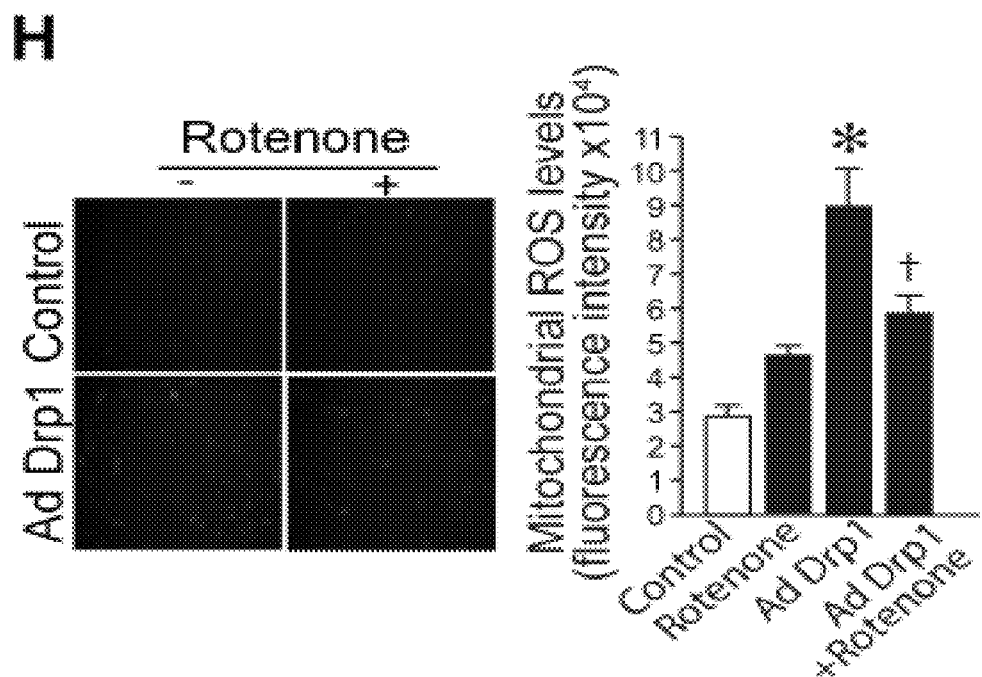

The overexpression of Drp1 using an adenoviral vector (FIG. 2A) increases mitochondrial fission (FIG. 2B). Cellular bioenergetics are disrupted (FIGS. 2C-2G) and mt-ROS levels from Complex I are increased (FIG. 2H).

The genotype of rs7312580, a regulatory promoter SNP in DNM1L gene (Drp1) in a well phenotyped ARDS/ICU cohort (n=437) with a medium age of 57, 54% male, and 26% 30-day mortality, was examined. This regulatory DNM1L SNP is significantly associated with inflammatory cytokine balance IL6/IL10 ratio (Table 1). Compared to an age- and ethnicity-matched control cohort, rs7312580 is significantly associated with ARDS/VILI susceptibility (adjusted $p<0.05$). These data suggest DNM1L is genetically associated with ARDS susceptibility and severity.

TABLE 1 rs7312580 genotype and clinical phenotypes (median)

| Genotype | CC (n = 205) | CG (n = 192) | GG (n = 40) | p-value |
| --- | --- | --- | --- | --- |
| SOFA Score | 7.0 | 7.0 | 6.0 | 0.12 |
| $PaO_2/FiO_2$ | 175 | 164 | 162 | 0.39 |
| Ang2 | 7.2e3 | 7.1e3 | 1.1e4 | 0.24 |

TABLE 1-continued

| rs7312580 genotype and clinical phenotypes (median) | | | | |
|---|---|---|---|---|
| Genotype | CC (n = 205) | CG (n = 192) | GG (n = 40) | p-value |
| IL-6 | 61.4 | 51.5 | 195.5 | 0.13 |
| IL-10 | 1.0 | 1.0 | 1.4 | 0.25 |
| IL6/IL10 | 58.5 | 53.6 | 194.3 | 0.03 |

To validate Drp1 as a therapeutic target, four preclinical VILI/ARDS models are used: i) VILI; ii) a "two-hit" model of polymicrobial sepsis (cecal ligation and puncture, CLP) in addition to mechanical ventilation; iii) a "two-hit" COV19-pneumonia model consisting of the delivery of the COVID19 spike protein combined with mechanical ventilation and iv) the ARDS-like extended lung inflammation model in which the mice are exposed long-term to LPS. Therapeutic agents are given before the initiation of injury in the VILI-only model or at the beginning of mechanical ventilation in the "two-hit" models, or 4 d after LPS exposure in the extended lung inflammation model to mimic the situation of a critically ill patient in the ICU.

Figures 3A, 3B:
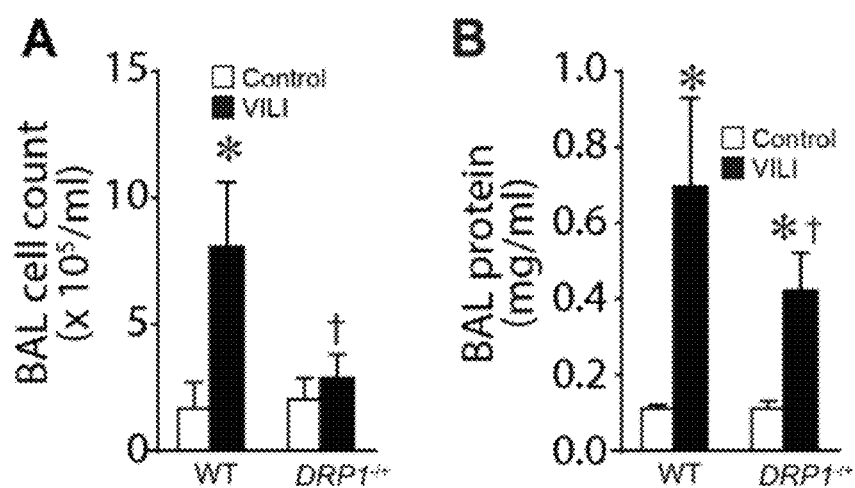
FIGS. 3A-3D show that Drp1+ mice are protected against VILI. Wildtype (WT) and heterozygous (Drp1−/+) Drp1 mice were subjected or not (spontaneous breathing) to high tidal mechanical ventilation (40 ml/kg, PEEP=5 cm $H_2O$, BR=75 bpm, 4 h). The increase in total cell counts (3A) and protein (3B) in the bronchoalveolar lavage (BAL) fluid is significantly reduced in Drp1+ mice. Evans Blue dye extravasation is also reduced in Drp1$^{-/+}$ mice (3C) and the lung injury score is attenuated (3D). Values are mean±SEM, n=4. * P<0.05 vs. spontaneously breathing control, †P<0.05 vs. WT+VILI.
Figure 3C:
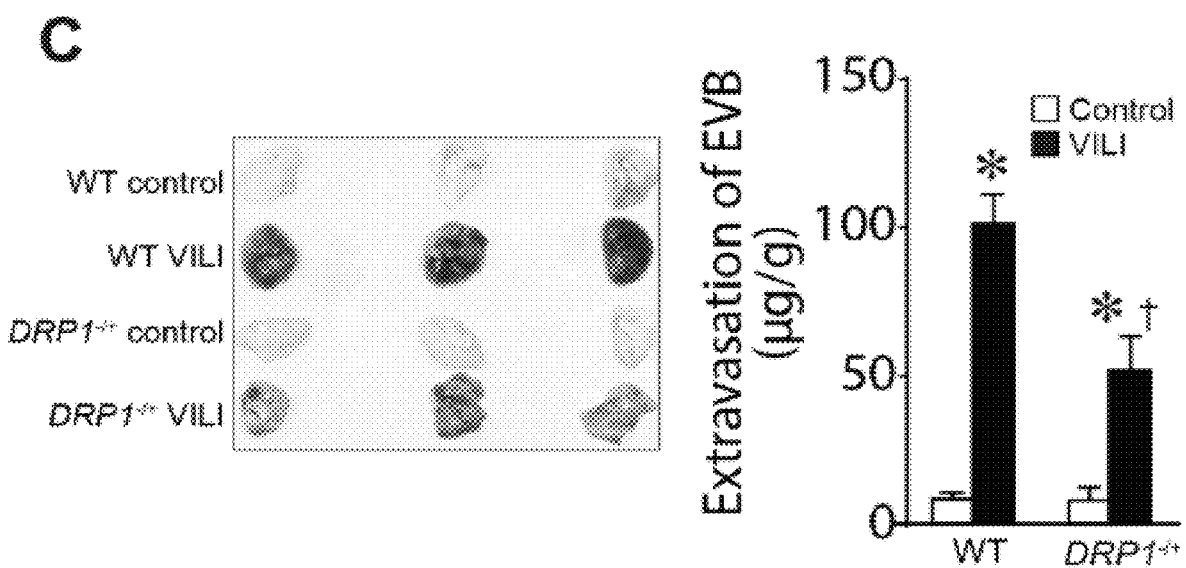
Figure 3D:
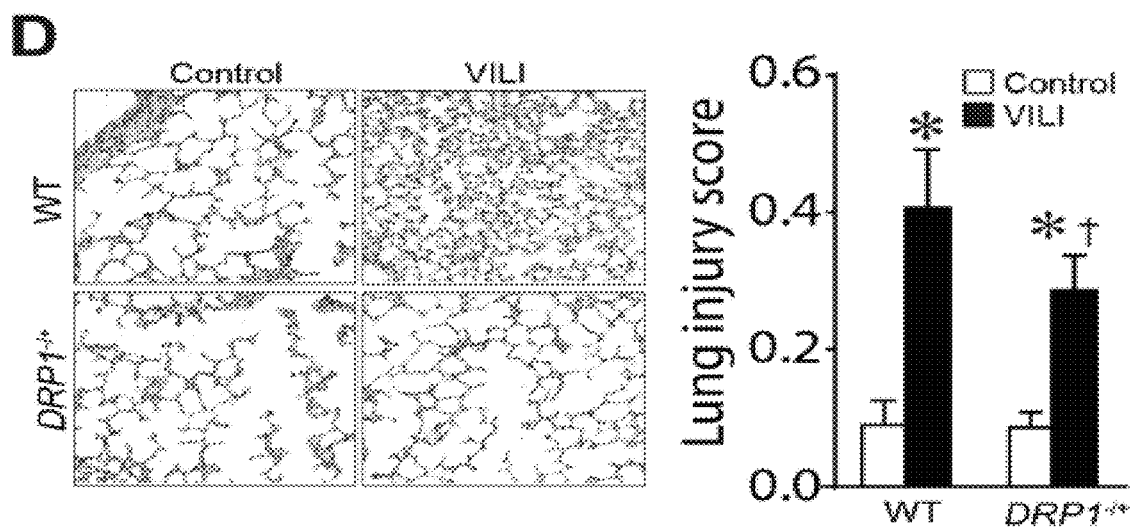

To decrease mitochondrial fission, a specific Drp1 siRNA was delivered in global heterozygote DNM1L (Drp1−/+) mice via JetPEI-mediated tail vein injections. Wildtype or global Drp1 heterozygous (Drp1−/+) mice were exposed to high tidal mechanical ventilation (HTV) to induce VILI. VILI is associated with increased endothelial permeability as shown by increased total cells (FIG. 3A) and protein (FIG. 3B) in the BALF as well as increased Evans Blue Dye extravasation (FIG. 3C). This results in lung injury (FIG. 3D). All these parameters are attenuated in Drp1−/+ mice confirming Drp1 as a therapeutic target against VILI.

Example 2—Drp1 Inhibitors as Therapy for VILI/ARDS

Small molecules reducing Drp1 function were identified to be used as a disease-modifying therapy for VILI/ARDS. After screening, 13 compounds were identified with a partial Drp1 inhibitory property at 10 µM. These compounds include:

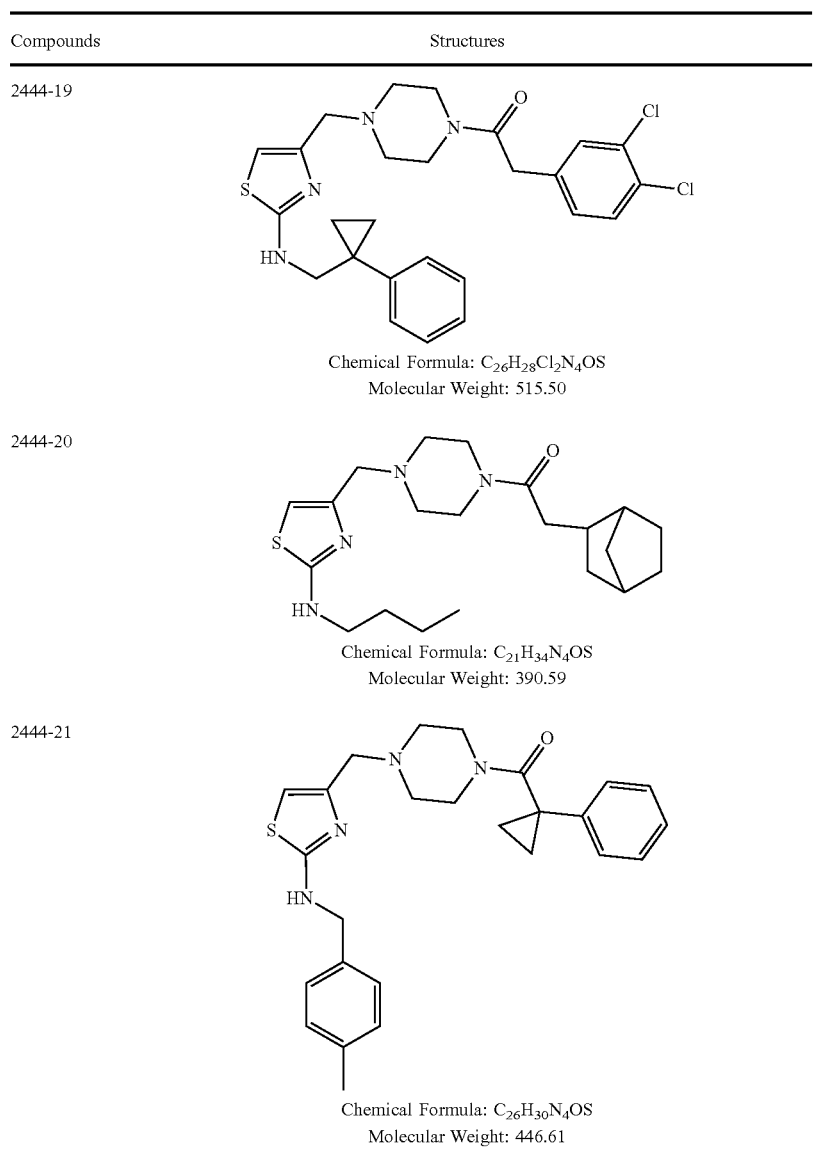

| Compounds | Structures |
|---|---|
| 2444-19 | Chemical Formula: $C_{26}H_{28}Cl_2N_4OS$<br>Molecular Weight: 515.50 |
| 2444-20 | Chemical Formula: $C_{21}H_{34}N_4OS$<br>Molecular Weight: 390.59 |
| 2444-21 | Chemical Formula: $C_{26}H_{30}N_4OS$<br>Molecular Weight: 446.61 |

| Compounds | Structures |
|---|---|
| 2444-24 | 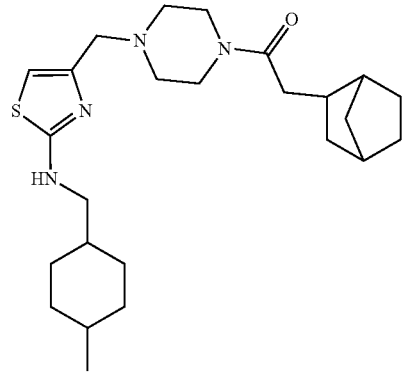 [SMILES: CC1CCC(CNc2nc(CN3CCN(C(=O)CC4CC5CCC4C5)CC3)cs2)CC1]<br>Chemical Formula: C$_{25}$H$_{40}$N$_4$OS<br>Molecular Weight: 444.68 |
| 2444-28 | 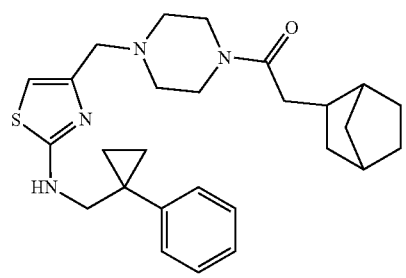 [SMILES: O=C(CC1CC2CCC1C2)N1CCN(Cc2csc(NCC3(c4ccccc4)CC3)n2)CC1]<br>Chemical Formula: C$_{27}$H$_{36}$N$_4$OS<br>Molecular Weight: 464.67 |
| 2444-31 | 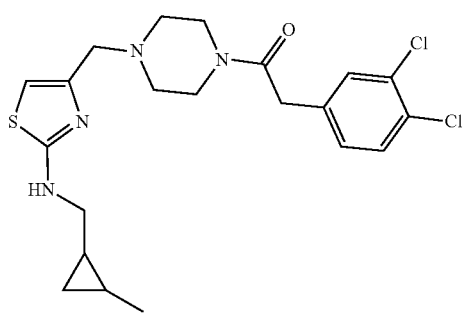 [SMILES: CC1CC1CNc1nc(CN2CCN(C(=O)Cc3ccc(Cl)c(Cl)c3)CC2)cs1]<br>Chemical Formula: C$_{21}$H$_{26}$Cl$_2$N$_4$OS<br>Molecular Weight: 453.43 |
| 2444-32 | 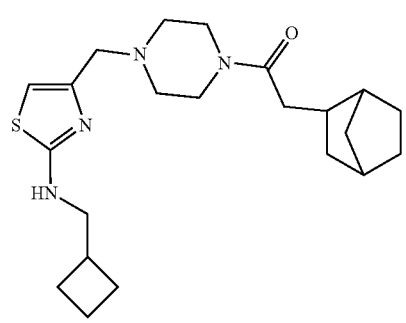 [SMILES: O=C(CC1CC2CCC1C2)N1CCN(Cc2csc(NCC3CCC3)n2)CC1]<br>Chemical Formula: C$_{22}$H$_{34}$N$_4$OS<br>Molecular Weight: 402.60 |

| Compounds | Structures |
|---|---|
| 2503-1 | 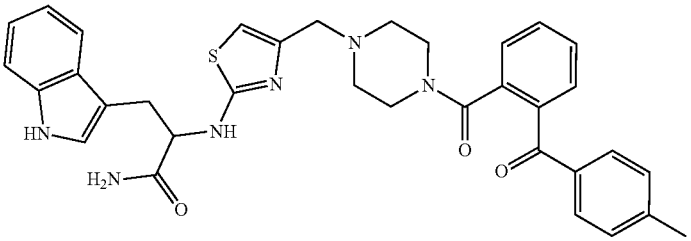 [SMILES: Cc1ccc(C(=O)c2ccccc2C(=O)N2CCN(Cc3csc(NC(Cc4c[nH]c5ccccc45)C(N)=O)n3)CC2)cc1]<br>Chemical Formula: $C_{34}H_{34}N_6O_3S$<br>Molecular Weight: 606.74 |

Figure 4:
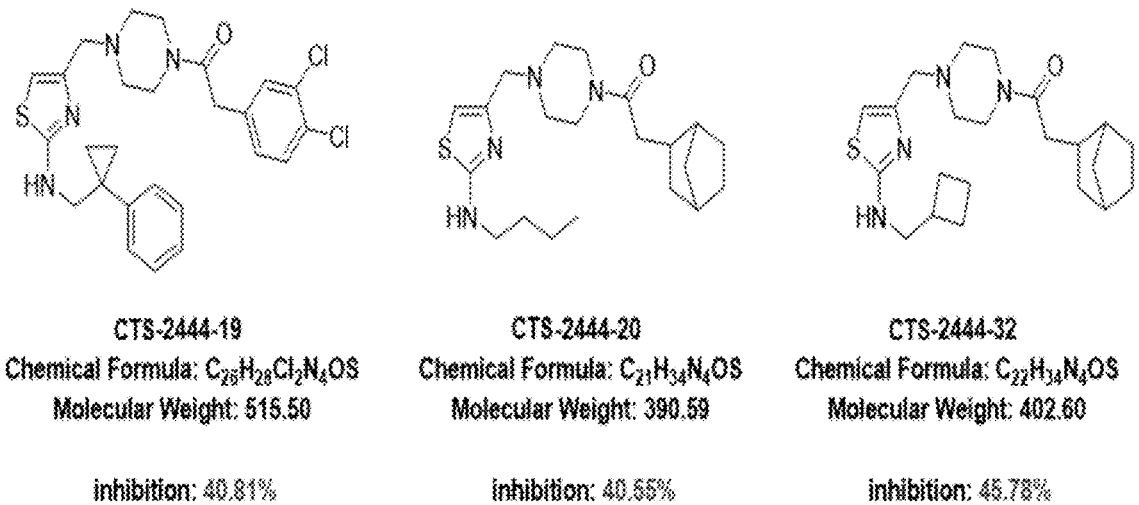
FIG. 4 shows compounds with Drp1 GTPase inhibitory property.

Three lead compounds (FIG. 4) were selected for further testing. These compounds are referred to as CTS (Center for Translational Science) 2444-19, CTS2444-20, and CTS2444-32. These compounds were examined for their ability to prevent eNAMPT-mediated mitochondrial fission.

Figure 5A:
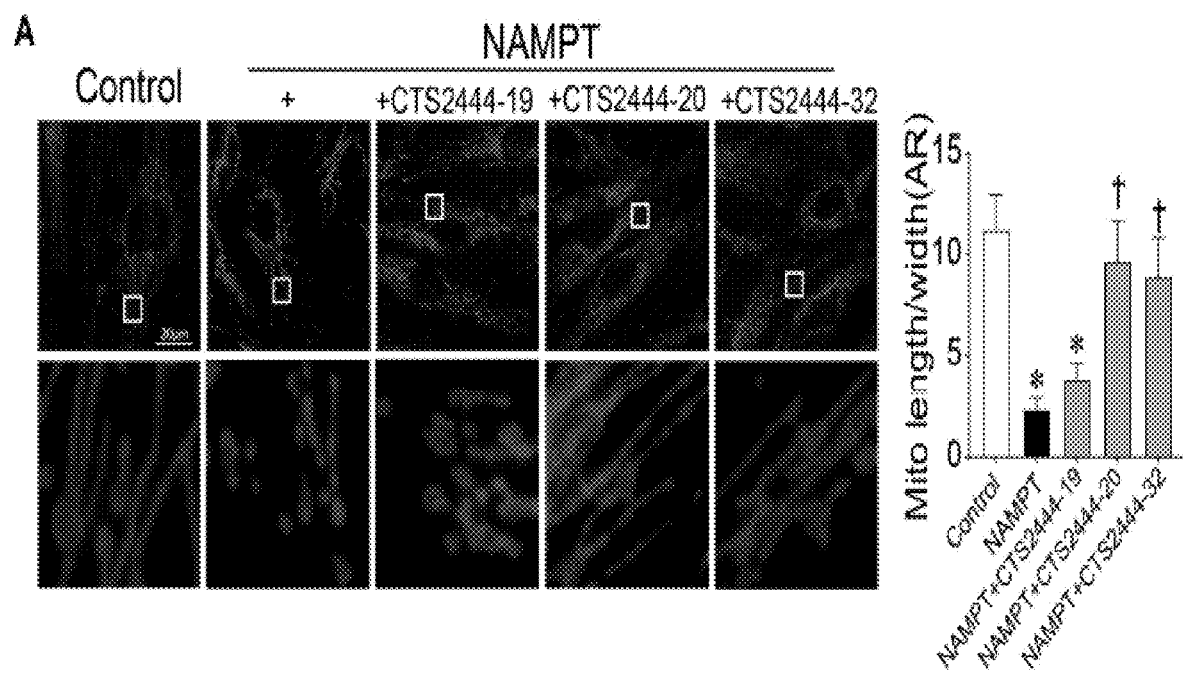
Figure 6D:
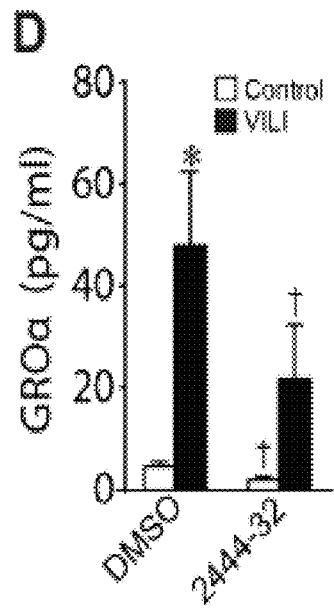
Figure 6E:
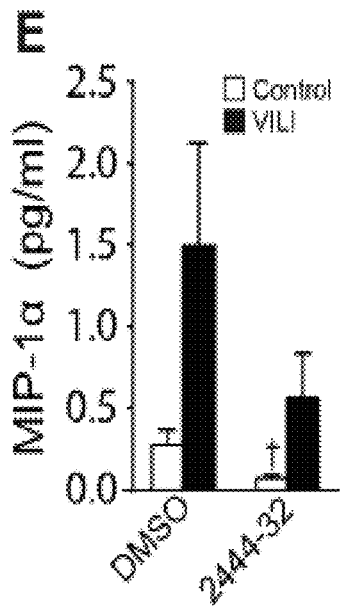
Figure 6F:
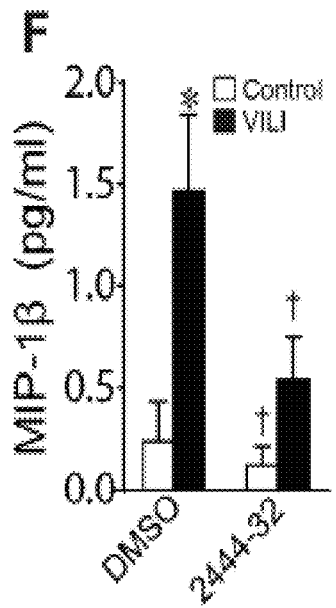
Figure 6G:
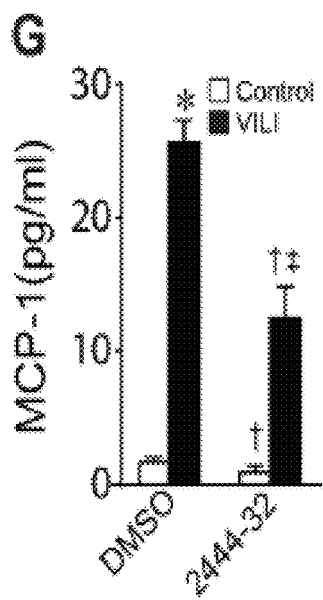
Figure 6H:
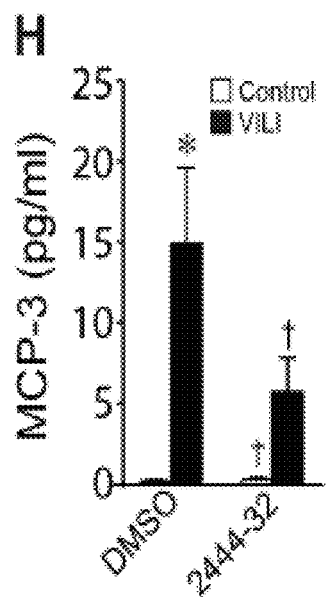
Figure 6I:
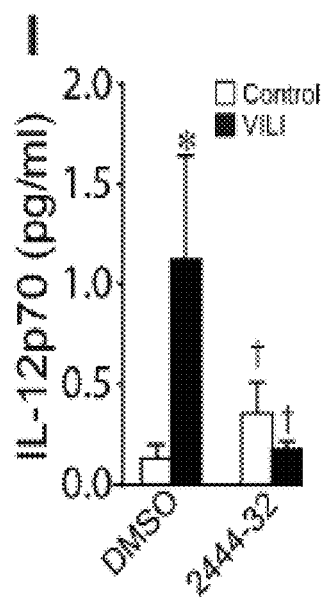

The results show that CTS 2444-20 and CTS 2444-32, but not CTS 2444-19, prevent the increase in fission induced by eNAMPT (FIG. 5A). CTS 2444-32 decreases lung injury in mice exposed to VILI (FIGS. 5B and 5C). In addition, CTS 2444-32 also attenuated the VILI-mediated increase in inflammatory cytokines in the BALF (FIG. 6), for example, TNFα (FIG. 6A), IL-6 (FIG. 6B), IL-18 (FIG. 6C), GROα, (FIG. 6D), MIP-1α (FIG. 6E), MIP-1β (FIG. 6F), MCP-1 (FIG. 6G), MCP-3 (FIG. 6H), and IL-12p70 (FIG. 6I).

Example 3—Drp1 Inhibitors as Therapy for Parkinson's Disease

Figure 7:
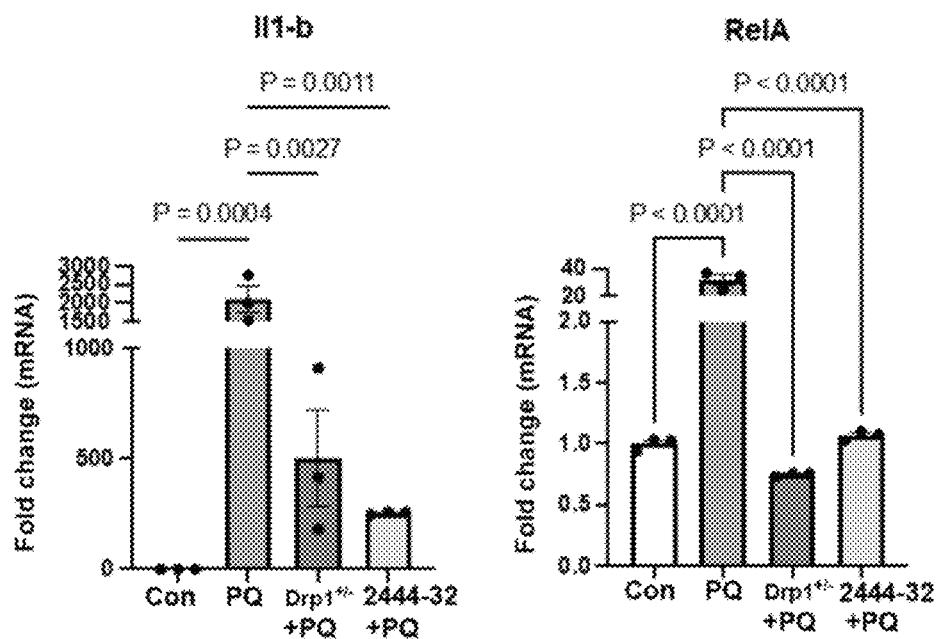
FIG. 7 shows the protective effect of compound 2444-32 in neuroinflammation. Microglia cells were treated with paraquat (PQ) in the presence or absence of compound 2444-32. The mRNA levels of IL-1β and RelA were analyzed. Microglia isolated from Drp1+/− pups was used as a positive control.

Neuroinflammation is commonly observed in Parkinson's disease (PD) and other neurodegenerative diseases. The role of activated microglia in causing neuroinflammation by upregulating the levels of pro-inflammatory cytokines such as IL-1β and relA is implicated in PD. The protective effects of one lead compound (2444-32) was evaluated using mouse primary microglia isolated from newborn pups. As shown in the FIG. 7, these cells were treated for with paraquat (PQ), a herbicide that has been linked to increasing the risk of developing PD, in the presence or absence of compound 2444-32. After 6 h, RNA was isolated for qPCR analysis. There was a dramatic increase in the levels of IL-1β and RelA mRNA. However, this increase was significantly attenuated in the cells treated with compound 2444-32. As a positive control model for a partial loss of Drp1 function, microglia isolated from Drp1+/− pups was used, which express approximately 50% of Drp1 as compared to their wild-type littermates. Significant reduction in neuroinflammation was also detected in these mutant microglia treated with PQ, indicating the protective effects of 2444-32 was most likely mediated through reduced Drp1 function, not off-target effects.

α-synuclein, a central component of the Lewy Bodies, is encoded by SNCA, which is the most investigated PD-linked gene to date. Accumulation of α-synuclein aggregates is a key pathological feature of PD. In addition to familial PD, α-synuclein is a key factor of idiopathic PD and other α-synucleinopathies such as dementia with Lewy bodies, and multiple-system atrophy. α-synuclein also play a role in Alzheimer's disease. Thus, the significance and impact of pathogenic α-synuclein extend beyond PD. Therefore, reducing α-synuclein pathology is a major therapeutic strategy for these neurological disorders.

Figure 8:
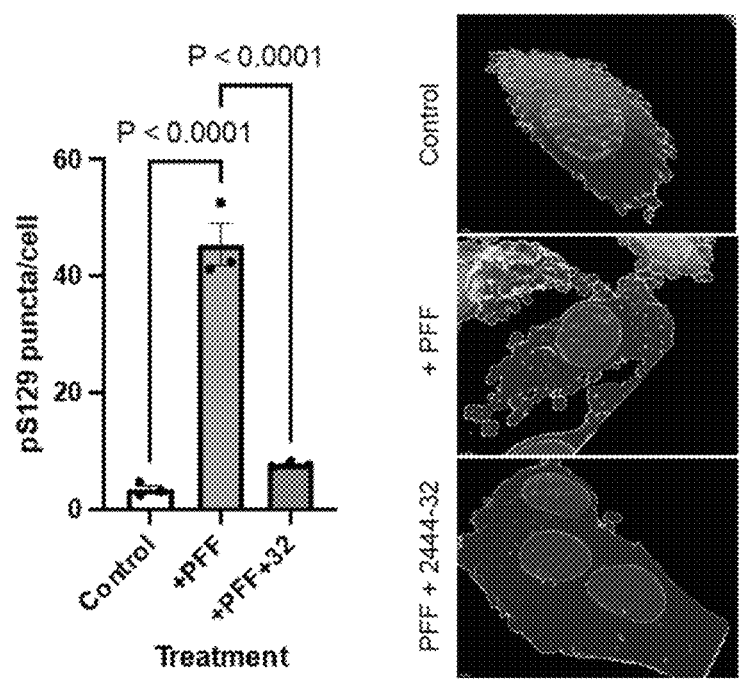
FIG. 8 shows the therapeutic effect of compound 2444-32 against α-synuclein. Human dopaminergic neuronal cells (LUHMES cells) were treated with human α-synuclein pre-formed fibrils (PFF), followed by the incubation with 20 μM of compound 2444-32 or vehicle control. α-synuclein aggregation is shows as puncta. These results demonstrate that compound 2444-32 is highly effective in reducing protein aggregation, which is a prominent feature in Parkinson's disease and other brain disorders.

To determine the therapeutic potential of compound 2444-32 against α-synuclein, human dopaminergic neuronal cells (LUHMES cells) were treated with human α-synuclein pre-formed fibrils (PFF). After 24 h incubation, cell culture media containing PFF was removed and replaced with fresh media containing 20 μM of compound 2444-32 or vehicle control. Cells were incubated for a further 48 h before having media removed and processed for immunostaining for pS129 α-synuclein, a pathogenic form of α-synuclein. α-synuclein protein aggregates were then quantified using the IMARIS (Oxford instruments) software. As shown in the FIG. 8, PFF treatment drastically increased α-synuclein aggregation (puncta), which is significantly reduced in the presence of compound 2444-32.

These results indicate that Drp1 inhibitor can be used as a therapy for Parkinson's disease.

Further, the three lead compounds were selected to validate in the models of acute lung injury.

In summary, new therapeutic approaches targeting mitochondrial network dynamics will result in the development of precise, individualized therapies.

All patents, patent applications, provisional applications, and publications referred to or cited herein are incorporated by reference in their entirety, including all figures and tables, to the extent they are not inconsistent with the explicit teachings of this specification.

It should be understood that the examples and embodiments described herein are for illustrative purposes only and that various modifications or changes in light thereof will be suggested to persons skilled in the art and are to be included within the spirit and purview of this application.

We claim:

1. A compound having a structure of:

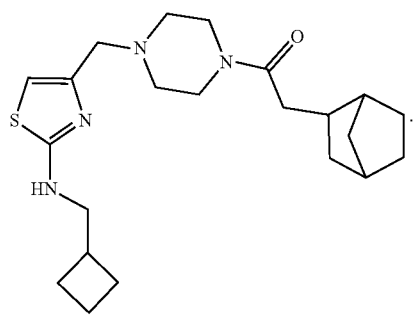 [SMILES: O=C(CC1CC2CCC1C2)N1CCN(Cc2csc(NCC3CCC3)n2)CC1 ; "."]

2. A composition comprising the compound according to claim 1, and a pharmaceutically acceptable carrier.

* * * * *